US008486640B2

(12) United States Patent
Fleshner et al.

(10) Patent No.: US 8,486,640 B2
(45) Date of Patent: Jul. 16, 2013

(54) ILEAL POUCH-ANAL ANASTOMOSIS (IPAA) FACTORS IN THE TREATMENT OF INFLAMMATORY BOWEL DISEASE

(75) Inventors: Phillip R. Fleshner, Los Angeles, CA (US); Eric A. Vasiliauskas, Manhattan Beach, CA (US); Gil Melmed, Los Angeles, CA (US); Stephan R. Targan, Santa Monica, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 12/530,390

(22) PCT Filed: Mar. 21, 2008

(86) PCT No.: PCT/US2008/057820
§ 371 (c)(1),
(2), (4) Date: Sep. 8, 2009

(87) PCT Pub. No.: WO2008/116150
PCT Pub. Date: Sep. 25, 2008

(65) Prior Publication Data
US 2010/0105044 A1    Apr. 29, 2010

Related U.S. Application Data

(60) Provisional application No. 60/896,171, filed on Mar. 21, 2007.

(51) Int. Cl.
*G01N 33/53* (2006.01)
*G01N 33/567* (2006.01)

(52) U.S. Cl.
USPC ............................ 435/7.1; 435/7.21; 436/501

(58) Field of Classification Search
None
See application file for complete search history.

(56) References Cited

U.S. PATENT DOCUMENTS

| | | | |
|---|---|---|---|
| 3,654,090 A | 4/1972 | Schuurs et al. |
| 3,850,752 A | 11/1974 | Schuurs et al. |
| 4,016,043 A | 4/1977 | Schuurs et al. |
| 4,265,823 A | 5/1981 | Nobile |
| 4,698,195 A | 10/1987 | Okumura et al. |
| 4,699,880 A | 10/1987 | Goldstein |
| 4,704,692 A | 11/1987 | Ladner |
| 4,800,159 A | 1/1989 | Mullis et al. |
| 4,880,548 A | 11/1989 | Pall et al. |
| 4,925,572 A | 5/1990 | Pall et al. |
| 4,935,234 A | 6/1990 | Todd et al. |
| 5,002,873 A | 3/1991 | St. John et al. |
| 5,085,318 A | 2/1992 | Leverick |
| 5,091,302 A | 2/1992 | Newman et al. |
| 5,114,842 A | 5/1992 | Plow et al. |
| 5,137,806 A | 8/1992 | Lemaistre et al. |
| 5,147,637 A | 9/1992 | Wright et al. |
| 5,210,015 A | 5/1993 | Gelfand et al. |
| 5,219,997 A | 6/1993 | Schlossman et al. |
| 5,227,369 A | 7/1993 | Rosen et al. |
| 5,234,810 A | 8/1993 | Kehrli, Jr. et al. |
| 5,235,049 A | 8/1993 | McClelland et al. |
| 5,236,081 A | 8/1993 | Fitzsimmons et al. |
| 5,264,554 A | 11/1993 | Newman |
| 5,272,263 A | 12/1993 | Hession et al. |
| 5,284,931 A | 2/1994 | Springer et al. |
| 5,491,063 A | 2/1996 | Fisher et al. |
| 5,494,920 A | 2/1996 | Glasebrook et al. |
| 5,518,488 A | 5/1996 | Schluger |
| 5,590,769 A | 1/1997 | Lin |
| 5,683,698 A | 11/1997 | Chavalli et al. |
| 5,691,151 A | 11/1997 | Braun et al. |
| 5,750,355 A | 5/1998 | Targan et al. |
| 5,830,675 A | 11/1998 | Targan et al. |
| 5,840,300 A | 11/1998 | Williams et al. |
| 5,874,233 A | 2/1999 | Targan et al. |
| 5,916,748 A | 6/1999 | Targan et al. |
| 5,937,862 A * | 8/1999 | Targan et al. .................. 128/898 |
| 5,942,390 A | 8/1999 | Comminelli et al. |
| 5,947,281 A | 9/1999 | Kaneff |
| 5,968,741 A | 10/1999 | Pievy et al. |
| 6,034,102 A | 3/2000 | Aiello |
| 6,074,835 A | 6/2000 | Braun et al. |
| 6,114,395 A | 9/2000 | Aiello |
| 6,183,951 B1 | 2/2001 | Plevy et al. |
| 6,348,316 B1 * | 2/2002 | Taylor et al. ....................... 435/6 |
| 6,376,176 B1 | 4/2002 | Taylor et al. |
| 6,406,701 B1 | 6/2002 | Pulido-Cejundo |

(Continued)

FOREIGN PATENT DOCUMENTS

AU   698604   2/1999
EP   0 760 010 B1   10/2002

(Continued)

OTHER PUBLICATIONS

Fleshner et al., Gut. Nov. 2001;49(5):671-677.*
Lodes, M.J. et al., Bacterial flagellin is a dominant antigen in Crohn disease, The Journal of Clinical Investigation, May 2004, 113:9, pp. 1296-1306.
Ogura, Y. et al., A frameshift mutation in NOD2 associated with susceptibility to Crohn's disease, Nature, 2001, vol. 411, pp. 603-606.
Targan, S.R. et al., Antibodies to a novel flagellin (CBir1) define a unique serologic response in Crohn's disease (CD), Gastroenterology, Elsevier, Philadelphia, PA, Apr. 2004, 126:4, Supp. 2, p. A113, XP009098183.
Targan, S.R. et al., Antibodies to CBir1 flagellin define a unique response that is associated independently with complicated Crohn's disease, Gastroenterology, 2005, 128:2020-2028.

(Continued)

*Primary Examiner* — Daniel C Gamett
(74) *Attorney, Agent, or Firm* — Sean D. Senn; Nixon Peabody LLP

(57) ABSTRACT

A common long term problem after Ileal Pouch-Anal Anastomosis (IPAA) is the inflammation of the pouch, called pouchitis. Additionally, about 5-10% of patients undergoing IPAA with a diagnosis of ulcerative colitis at the time of surgery are subsequently diagnosed with Crohn's disease. In one embodiment, the present invention provides methods of diagnosing and predicting susceptibility to pouchitis after IPAA by detecting the presence or absence of pANCA and/or Cbir1 Flagellin expression.

3 Claims, No Drawings

U.S. PATENT DOCUMENTS

| | | | |
|---|---|---|---|
| 6,692,916 B2 | 2/2004 | Bevilacqua et al. | |
| 6,858,391 B2 | 2/2005 | Nunez et al. | |
| 6,869,762 B1 | 3/2005 | Daly et al. | |
| 7,138,237 B1 | 11/2006 | Targan et al. | |
| 7,252,971 B2 | 8/2007 | Benson et al. | |
| 7,332,156 B2 | 2/2008 | Bowman et al. | |
| 7,332,631 B2 | 2/2008 | Hogarth et al. | |
| 7,361,733 B2 * | 4/2008 | Hershberg et al. | 530/350 |
| 7,759,079 B2 * | 7/2010 | Oh et al. | 435/7.31 |
| 2001/0006789 A1 | 7/2001 | Maino et al. | |
| 2002/0006613 A1 | 1/2002 | Shyjan et al. | |
| 2002/0048566 A1 | 4/2002 | El-Diery et al. | |
| 2002/0106684 A1 | 8/2002 | Kopreski | |
| 2002/0150939 A1 | 10/2002 | Taylor et al. | |
| 2002/0019837 A1 | 12/2002 | Wang et al. | |
| 2003/0092019 A1 | 5/2003 | Meyer et al. | |
| 2003/0129215 A1 | 7/2003 | Mollison et al. | |
| 2003/0138781 A1 | 7/2003 | Whitehead | |
| 2003/0148345 A1 | 8/2003 | Kopreski | |
| 2003/0176409 A1 | 9/2003 | Offner | |
| 2003/0198640 A1 | 10/2003 | Yu et al. | |
| 2004/0053262 A1 | 3/2004 | Lu | |
| 2004/0181048 A1 | 9/2004 | Wang et al. | |
| 2004/0203076 A1 | 10/2004 | Targan et al. | |
| 2004/0213761 A1 | 10/2004 | Bowman et al. | |
| 2004/0219555 A1 | 11/2004 | Van Heel | |
| 2004/0265864 A1 | 12/2004 | Mitsuhashi | |
| 2005/0054021 A1 | 3/2005 | Targan et al. | |
| 2005/0143333 A1 | 6/2005 | Richards et al. | |
| 2005/0163764 A1 | 7/2005 | Medzhitov et al. | |
| 2005/0182007 A1 | 8/2005 | McSwiggen et al. | |
| 2005/0261219 A1 | 11/2005 | Richards et al. | |
| 2006/0003392 A1 | 1/2006 | Oh et al. | |
| 2006/0067936 A1 | 3/2006 | Benson et al. | |
| 2006/0141478 A1 | 6/2006 | Brant et al. | |
| 2006/0154276 A1 | 7/2006 | Lois et al. | |
| 2006/0211020 A1 | 9/2006 | Farrer et al. | |
| 2007/0037165 A1 | 2/2007 | Venter et al. | |
| 2007/0059758 A1 | 3/2007 | Levine et al. | |
| 2007/0072180 A1 | 3/2007 | Abreu et al. | |
| 2007/0196835 A1 | 8/2007 | Bankaitis-Davis et al. | |
| 2007/0254850 A1 | 11/2007 | Lieberman et al. | |
| 2007/0275424 A1 | 11/2007 | Gewirtz et al. | |
| 2008/0038831 A1 | 2/2008 | Benson et al. | |
| 2008/0081822 A1 | 4/2008 | Berry et al. | |
| 2008/0091471 A1 | 4/2008 | Michon et al. | |
| 2008/0095775 A1 | 4/2008 | Lewis et al. | |
| 2008/0103180 A1 | 5/2008 | Fleming et al. | |
| 2008/0108713 A1 | 5/2008 | Begovich et al. | |
| 2008/0131887 A1 | 6/2008 | Stephan et al. | |
| 2008/0206762 A1 | 8/2008 | Ferrer Abizanda et al. | |
| 2008/0261207 A1 | 10/2008 | Mitsuhashi | |
| 2008/0293582 A1 | 11/2008 | Li et al. | |
| 2009/0099789 A1 | 4/2009 | Stephan et al. | |
| 2009/0180380 A1 | 7/2009 | Prabhakar et al. | |
| 2009/0253133 A1 | 10/2009 | Mitsuhashi et al. | |
| 2009/0297563 A1 | 12/2009 | Borglum et al. | |
| 2010/0015156 A1 | 1/2010 | Dubinsky et al. | |
| 2010/0021455 A1 | 1/2010 | Targan et al. | |
| 2010/0021917 A1 | 1/2010 | Rotter et al. | |
| 2010/0055700 A1 | 3/2010 | Targan et al. | |
| 2010/0105044 A1 | 4/2010 | Fleshner et al. | |
| 2010/0144903 A1 | 6/2010 | Taylor et al. | |
| 2010/0184050 A1 | 7/2010 | Rotter et al. | |
| 2010/0190162 A1 | 7/2010 | Rotter et al. | |
| 2010/0240043 A1 | 9/2010 | Rotter et al. | |
| 2010/0284999 A1 | 11/2010 | Taylor et al. | |
| 2011/0124644 A1 | 5/2011 | Targan et al. | |
| 2011/0177969 A1 | 7/2011 | Rotter et al. | |
| 2011/0189685 A1 | 8/2011 | Taylor et al. | |
| 2011/0229471 A1 | 9/2011 | Rotter et al. | |

FOREIGN PATENT DOCUMENTS

| | | |
|---|---|---|
| EP | 1285271 B1 | 2/2003 |
| EP | 1 285 271 B1 | 8/2005 |
| EP | 1 243 274 B1 | 6/2008 |
| EP | 1 819 827 B1 | 8/2010 |
| EP | 2 270 512 A1 | 1/2011 |
| WO | WO 91-16928 | 4/1991 |
| WO | WO 92-02819 | 7/1991 |
| WO | WO 92-22323 | 6/1992 |
| WO | WO 93-07485 | 4/1993 |
| WO | WO 93-12248 | 6/1993 |
| WO | WO 94-04188 | 3/1994 |
| WO | WO 95-21941 | 8/1995 |
| WO | WO 95-31575 | 11/1995 |
| WO | WO 97-25445 | 7/1997 |
| WO | WO 98-47004 | 4/1998 |
| WO | WO 00-76492 | 12/2000 |
| WO | WO 01-20036 | 3/2001 |
| WO | WO 03-040404 | 5/2003 |
| WO | WO 03-053220 | 7/2003 |
| WO | WO 03-059333 | 7/2003 |
| WO | WO 03-090694 | 11/2003 |
| WO | WO 03-099312 | 12/2003 |
| WO | WO 2004-020968 | 3/2004 |
| WO | WO 2004-031159 | 4/2004 |
| WO | 2004/048600 A2 | 6/2004 |
| WO | WO 2004-048600 | 6/2004 |
| WO | WO 2005-044792 | 5/2005 |
| WO | WO 2005-114469 | 12/2005 |
| WO | WO 2005-115115 | 12/2005 |
| WO | WO 2005-116251 | 12/2005 |
| WO | WO 2006-063093 | 6/2006 |
| WO | WO 2006-110091 | 10/2006 |
| WO | WO 2006-116721 | 11/2006 |
| WO | WO 2007-025989 | 3/2007 |
| WO | WO 2007-117611 | 10/2007 |
| WO | WO 2008-048984 | 4/2008 |
| WO | WO 2008-101133 | 8/2008 |
| WO | WO 2008-106451 | 9/2008 |
| WO | WO 2008-106579 | 9/2008 |
| WO | WO 2008-109782 | 9/2008 |
| WO | WO 2008-112990 | 9/2008 |
| WO | WO 2008-116150 | 9/2008 |
| WO | WO 2008-134569 | 11/2008 |
| WO | WO 2008-137762 | 11/2008 |
| WO | WO 2008-141148 | 11/2008 |
| WO | WO 2009-052512 | 4/2009 |
| WO | WO 2009-143278 | 11/2009 |
| WO | WO 2010-039931 | 4/2010 |
| WO | WO 2010-048415 | 4/2010 |
| WO | WO 2010-062960 | 6/2010 |
| WO | WO 2010-075579 | 7/2010 |
| WO | WO 2010-075584 | 7/2010 |
| WO | WO 2011-017120 | 2/2011 |
| WO | WO 2011-088237 | 7/2011 |
| WO | WO 2011-088306 | 7/2011 |
| WO | WO 2011-088380 | 7/2011 |

OTHER PUBLICATIONS

Vermeire, S. et al., Current status of genetics research in inflammatory bowel disease, Genes and Immunity, 2005, 6:637-645.
Examination Report dated Jul. 8, 2010 for Australian patent application No. 2005314089, 2 pages.
Australia Office Action in App. No. 2005314089 dated Jul. 8, 2010 (Exhibit 56).
Australia Office Action in App. No. 26384/95 dated Sep. 19, 1997 (Exhibit 57).
Australia Office Action in App. No. 13576/1997 dated Sep. 7, 2000 (Exhibit 58).
Australia Office Action in App. No. 13576/1997 dated Jul. 20, 2000 (Exhibit 59).
Australia Office Action in App. No. 13576/1997 dated Jul. 7, 1999 (Exhibit 60).
Canada Office Action in App. No. 13576/97 dated Jul. 7, 1999 (Exhibit 61).
Canada Office Action in App. No. 2,183,147 dated Jun. 20, 2007 (Exhibit 62).
Canada Office Action in App. No. 2,183,147 dated Mar. 20, 2006 (Exhibit 63).
Canada Office Action in App. No. 2,183,147 dated Apr. 1, 2005 (Exhibit 64).
Canada Office Action in App. No. 2,589,746 dated May 9, 2011 (Exhibit 65).

Canada Office Action in App. No. 2,589,746 dated Aug. 3, 2010 (Exhibit 66).
Europe Office Action in 05 853 294 dated May 8, 2008 (Exhibit 67).
European Search Report in 05 85 3294 dated Apr. 29, 2008 (Exhibit 69).
European Search Report in 1 017 1757 dated Nov. 10, 2010 (Exhibit 70).
European Search Report in 95 921 264.8 dated Feb. 24, 1999 (Exhibit 71).
European Search Report in 95 921 264.8 dated Feb. 29, 2000 (Exhibit 72).
Further Examination Report in 05 85 3294 dated Apr. 30, 2009 (Exhibit 73).
IPER for PCT/US1995/001434 dated May 22, 1996 (Exhibit 74).
IPER for PCT/US1995/06107 dated May 6, 1996 (Exhibit 75).
IPER for PCT/US2000/025112 dated Dec. 20, 2001 (Exhibit 76).
IPER for PCT/US2003/023926 dated Aug. 19, 2004 (Exhibit 77).
IPER for PCT/US2005/044335 dated Jun. 13, 2007 (Exhibit 78).
IPRP for PCT/US2008/057820 dated Sep. 11, 2009 (Exhibit 79).
IPRP for PCT/US2008/063202 dated Sep. 11, 2009 (Exhibit 80).
IPRP for PCT/US1997/00042 dated Apr. 1, 1998 (Exhibit 81).
IPRP for PCT/US2005/018161 dated Jun. 4, 2008 (Exhibit 82).
IPRP for PCT/US2007/008597 dated Oct. 8, 2008 (Exhibit 83).
IPRP for PCT/US2008/057028 dated Sep. 15, 2009 (Exhibit 84).
IPRP for PCT/US2008/054033 dated Aug. 21, 2008 (Exhibit 85).
IPRP for PCT/US2008/055020 dated Aug. 26, 2009 (Exhibit 86).
IPRP for PCT/US2008/055236 dated Sep. 1, 2009 (Exhibit 87).
IPRP for PCT/US2008/056103 dated Sep. 3, 2008 (Exhibit 88).
IPRP for PCT/US2008/061652 dated Dec. 1, 2008 (Exhibit 89).
IPRP for PCT/US2008/062531 dated Nov. 10, 2009 (Exhibit 90).
IPRP for PCT/US2008/080526 dated Apr. 20, 2010 (Exhibit 91).
IPRP for PCT/US2009/044720 dated Nov. 23, 2010 (Exhibit 92).
IPRP for PCT/US2009/059190 dated Apr. 5, 2011 (Exhibit 93).
IPRP for PCT/US2009/061698 dated Apr. 26, 2011 (Exhibit 94).
IPRP for PCT/US2009/065928 dated May 31, 2011 (Exhibit 95).
IPRP for PCT/US2009/069531 dated Jun. 29, 2011 (Exhibit 96).
IPRP for PCT/US2009/069541 dated Jun. 29, 2011 (Exhibit 97).
ISR for PCT/2008/057820 dated Sep. 11, 2008 (Exhibit 98).
ISR for PCT/2008/063202 dated Nov. 18, 2008 (Exhibit 99).
ISR for PCT/US1995/01434 dated Jul. 21, 1995 (Exhibit 100).
ISR for PCT/US1995/06107 dated Jun. 10, 1995 (Exhibit 101).
ISR for PCT/US1997/00042 dated Apr. 21, 1997 (Exhibit 102).
ISR for PCT/US2000/25112 dated Jun. 8, 2001 (Exhibit 103).
ISR for PCT/US2003/023926 dated Jun. 23, 2004 (Exhibit 104).
ISR for PCT/US2005/018161 dated Jun. 4, 2008 (Exhibit 105).
ISR for PCT/US2005/044335 dated Sep. 22, 2006 (Exhibit 106).
ISR for PCT/US2007/008597 dated Jun. 4, 2008 (Exhibit 107).
ISR for PCT/US2008/050728 dated Oct. 10, 2008 (Exhibit 108).
ISR for PCT/US2008/054033 dated Aug. 21, 2008 (Exhibit 109).
ISR for PCT/US2008/055020 dated Aug. 14, 2008 (Exhibit 110).
ISR for PCT/US2008/055236 dated Nov. 14, 2008 (Exhibit 111).
ISR for PCT/US2008/056103 dated Sep. 3, 2008 (Exhibit 112).
ISR for PCT/US2008/061652 dated Dec. 1, 2008 (Exhibit 113).
ISR for PCT/US2008/062531 dated Nov. 18, 2008 (Exhibit 114).
ISR for PCT/US2008/080526 dated Mar. 25, 2009 (Exhibit 115).
ISR for PCT/US2009/0044720 dated Nov. 5, 2009 (Exhibit 116).
ISR for PCT/US2009/059190 dated Mar. 16, 2010 (Exhibit 117).
ISR for PCT/US2009/061698 dated Mar. 16, 2010 (Exhibit 118).
ISR for PCT/US2009/065928 dated Aug. 3, 2010 (Exhibit 119).
ISR for PCT/US2009/069531 dated Aug. 4, 2010 (Exhibit 120).
ISR for PCT/US2009/0695341 dated Mar. 4, 2010 (Exhibit 121).
ISR for PCT/US2010/043427 dated Mar. 12, 2010 (Exhibit 122).
ISR for PCT/US2011//021180 dated Jun. 15, 2011 (Exhibit 123).
ISR for PCT/US2011/021382 dated Mar. 15, 2011 (Exhibit 124).
ISR for PCT/US2011/028694 dared Jul. 27, 2011 (Exhibit 125).
Notice of Allowance dated Apr. 29, 1999 for U.S. Appl. No. 08/798,668 dated Apr. 29, 1999 (Exhibit 126).
Notice of Allowance dated Mar. 19, 2002 for U.S. Appl. No. 09/419,406 dated Mar. 19, 2002 (Exhibit 127 ).
Office Action for U.S. Appl. No. 08/587,911 dated Apr. 15, 1997 (Exhibit 128).
Office Action for U.S. Appl. No. 08/587,911 dated Jan. 5, 1998 (Exhibit 129).
Office Action for U.S. Appl. No. 08/587,911 dated Jul. 6, 1998 (Exhibit 130).
Office Action for U.S. Appl. No. 11/720,785 dated Dec. 23, 2010 (Exhibit 131).
Office Action for U.S. Appl. No. 11/720,785 dated Jul. 19, 2010 (Exhibit 132).
Office Action for U.S. Appl. No. 12/528,055 dated Jun. 27, 2011 (Exhibit 133).
Office Action for U.S. Appl. No. 12/530,390 dated Mar. 25, 2011 (Exhibit 134).
Office Action for U.S. Appl. No. 12/599,549 dated Apr. 26, 2011 (Exhibit 135).
Office Action in U.S. Appl. No. 08/196,003 dated Dec. 12, 1995 (Exhibit 136).
Office Action in U.S. Appl. No. 08/196,003 dated Oct. 2, 1996 (Exhibit 137).
Office Action in U.S. Appl. No. 08/245,297 dated Mar. 15, 1995 (Exhibit 138).
Office Action in U.S. Appl. No. 08/245,297 dated Jan. 22, 1996 (Exhibit 139).
Office Action in U.S. Appl. No. 08/245,297 dated Jul. 11, 1996 (Exhibit 140).
Office Action in U.S. Appl. No. 08/245,297 dated Dec. 9, 1996 (Exhibit 141).
Office Action in U.S. Appl. No. 08/798,668 dated Jan. 29, 1998 (Exhibit 142).
Office Action in U.S. Appl. No. 08/798,668 dated Jun. 6, 1997 (Exhibit 143).
Office Action in U.S. Appl. No. 08/798,668 dated Aug. 10, 1998 (Exhibit 144).
Office Action in U.S. Appl. No. 08/798,668 dated Apr. 29, 1999 (Exhibit 145).
Office Action in U.S. Appl. No. 08/933,824 dated Apr. 14, 1998 (Exhibit 146).
Office Action in U.S. Appl. No. 08/933,824 dated Jan. 5, 1999 (Exhibit 147).
Office Action in U.S. Appl. No. 09/395,345 dated May 3, 2000 (Exhibit 148).
Office Action in U.S. Appl. No. 09/395,345 dated Nov. 21, 2000 (Exhibit 149).
Office Action in U.S. Appl. No. 09/395,345 dated May 9, 2001 (Exhibit 150).
Office Action in U.S. Appl. No. 09/419,406 dated Jul. 17, 2001 (Exhibit 151).
Office Action in U.S. Appl. No. 09/419,406 dated Dec. 28, 2001 (Exhibit 152).
Office Action in U.S. Appl. No. 09/419,406 dated Apr. 24, 2000 (Exhibit 153).
Office Action in U.S. Appl. No. 09/419,408 dated Feb. 1, 2001 (Exhibit 154).
Office Action in U.S. Appl. No. 09/419,408 dated May 30, 2002 (Exhibit 155).
Office Action in U.S. Appl. No. 09/419,408 dated Nov. 14, 2002 (Exhibit 156).
Office Action in U.S. Appl. No. 10/075,425 dated Oct. 1, 2004 (Exhibit 157).
Office Action in U.S. Appl. No. 10/075,425 dated Jun. 17, 2005 (Exhibit 158).
Office Action in U.S. Appl. No. 10/356,736 dated Jul. 7, 2005 (Exhibit 159).
Office Action in U.S. Appl. No. 10/356,736 dated Apr. 10, 2006 (Exhibit 160).
Office Action in U.S. Appl. No. 10/356,736 dated Apr. 26, 2007 (Exhibit 161).
Office Action in U.S. Appl. No. 10/356,736 dated Nov. 30, 2007 (Exhibit 162).
Office Action in U.S. Appl. No. 10/356,736 dated Aug. 14, 2008 (Exhibit 163).
Office Action in U.S. Appl. No. 10/526,256 dated Dec. 29, 2008 (Exhibit 164).
Office Action in U.S. Appl. No. 10/526,256 dated May 9, 2008 (Exhibit 165).

Office Action in U.S. Appl. No. 10/526,256 dated Aug. 25, 2009 (Exhibit 166).
Written Opinion for PCT/US1995/01434 dated Nov. 20, 1995 (Exhibit 167).
Written Opinion for PCT/US1995/06107 dated Dec. 2, 1996 (Exhibit 168).
Written Opinion for PCT/US1997/00042 dated Oct. 29, 1997 (Exhibit 169).
Written Opinion for PCT/US2005/018161 dated Jun. 4, 2008 (Exhibit 170).
Written Opinion for PCT/US2005/044335 dated Aug. 26, 2006 (Exhibit 171).
Written Opinion for PCT/US2007/008597 dated Jun. 4, 2008 (Exhibit 172).
Written Opinion for PCT/US2008/050728 dated Oct. 10, 2008 (Exhibit 173).
Written Opinion for PCT/US2008/054033 dated Aug. 21, 2008 (Exhibit 174).
Written Opinion for PCT/US2008/055020 dated Aug. 14, 2008 (Exhibit 175).
Written Opinion for PCT/US2008/055236 dated Nov. 14, 2008 (Exhibit 176).
Written Opinion for PCT/US2008/056103 dated Sep. 3, 2008 (Exhibit 177).
Written Opinion for PCT/US2008/057820 dated Aug. 26, 2008 (Exhibit 178).
Written Opinion for PCT/US2008/061652 dated Dec. 1, 2008 (Exhibit 179).
Written Opinion for PCT/US2008/062531 dated Nov. 18, 2008 (Exhibit 180).
Written Opinion for PCT/US2008/063202 dated Nov. 18, 2008 (Exhibit 181).
Written Opinion for PCT/US2008/080526 dated Mar. 25, 2009 (Exhibit 182).
Written Opinion for PCT/US2009/044720 dated Nov. 5, 2009 (Exhibit 183).
Written Opinion for PCT/US2009/059190 dated Mar. 16, 2010 (Exhibit 184 ).
Written Opinion for PCT/US2009/061698 dated Mar. 16, 2010 (Exhibit 185).
Written Opinion for PCT/US2009/065928 dated Aug. 3, 2010 (Exhibit 186).
Written Opinion for PCT/US2009/069531 dated Aug. 4, 2010 (Exhibit 187).
Written Opinion for PCT/US2009/069541 dated Mar. 4, 2010 (Exhibit 188).
Written Opinion for PCT/US2011/021382 dated Mar. 15, 2011 (Exhibit 189).
Written Opinion for PCT/US2011/028694 dated Jul. 27, 2011 (Exhibit 190).
Abraham et al., Haplotypic polymorphisms of the TNFB gene. *Immunogenetics* vol. 33 pp. 50-53 1991 (Exhibit 191).
Abreu et al., Mutations in NOD2 are associated with fibrostenosing disease in patients with Crohn's disease. *Gastroenterology* vol. 123 pp. 679-688 2002 (Exhibit 192).
Adam, Jamila et al., Immune response in cancer. *Pharmacology & Therapeutics* vol. 99 pp. 113-132 2003 (Exhibit 193).
Adams et al., 3400 new expressed sequence tags identify diversity of transcripts in the human brain. *Nature Genetics* vol. 4 pp. 256-267 1993 (Exhibit 194).
Agarwal, B. B. et al., The role of the TNF and its family members in inflammation and cancer: lessons from gene deletion. *Curr Drug Targets Inflamm Allergy* vol. 1 pp. 327-341 2002 (Exhibit 195).
Ahmad et al. The molecular classification of the clinical manifestations of Crohn's disease. *Gasterenterology* vol. 122 pp. 854-866 2002 (Exhibit 196).
Ajioka et al., Haplotype analysis of hemochromatosis: evaluation of linkage-disequilibrium approaches and evolution of disease chromosome. *Am J Hum Genet* vol. 60 pp. 1439-1447 1997 (Exhibit 197).
Akolkar et al., The IBD1 locus for susceptibility to Crohn's disease has a greater impack on Ashkenazi Jews with early onset diabetes. *Am J Gastroentrol* vol. 96 pp. 1127-1132 2001 (Exhibit 198).

Ames et al., Are vitamin and mineral deficiencies a major cancer risk? *Nature* vol. 694-704 2002 (Exhibit 199).
An et al., A tumor necrosis factor α-inducible promoter variant of interferon-g accelerates CD4+ Tcell depletion in human immunodeficiency virus-1 infected individuals. *J Infectious Diseases* vol. 188 pp. 228-213 2003 (Exhibit 200).
Ando et al. Triplet repeat polymorphism within the NOTCH4 gene located near the junction of the HLA class II and class III regions in narcolepsy. *Tissue Antigens* vol. 50 pp. 646-649 1997 (Exhibit 201).
Andus et al., Measurement of TNFalpha mRNA in a small number of cells by quantitative polymerase chain reaction (PCR) *Regional Immunology* vol. 5 pp. 11-17 1993 (Exhibit 202).
Annese et al., Genetic analysis in Italian families with inflammatory bowel disease supports linkage to the IBD1 locus—a GSIC study. *Eur J Hum Genet* vol. 7 pp. 567-573 1999 (Exhibit 204).
Aron et al., Analysis of shp70 gene polymorphism in allergic asthma *Allergy* vol. 54 pp. 165-170 1999 (Exhibit 205).
Ausubel, F. M. et al., Current protocols in Molecular Biology. Wiley Interscience, New York, 1987 1989 Book not included.
Badger et al., Idoxifene, a novel selective estrogen receptor modulator is effective in a rat model of adjuvant-induced arthritis. *J Pharmacology and Experimental Therapeutics* vol. 291 pp. 1380-1386 1999 (Exhibit 207).
Ballantyne, C. et al., Short communication, assignment of the gene for intercellular adhesion molecule-1 (ICAM-1) to proximal mouse chromosome 9. *Genomics* vol. 9 pp. 547-550 1991 (Exhibit 208).
Bao et al., Molecular mechanism for gender differences in susceptibility to T Cell mediated autoimmune diabetes in nonobese diabetic mice. *J of Immunol* vol. 168 pp. 5269-5379 2002 (Exhibit 209).
Becker et al., Clustering of non-major histocompatibility complex susceptibility candidate loci in human autoimmune disease. *Proc Natl Acad Sci.* vol. 95 pp. 9979-9984 1998 (Exhibit 210).
Benoit, R. et al., Presence of somatostatin-28-(1-12) in hypothalamus and pancreas. *Proc Natl Acad Sci. USA* vol. 79 pp. 917-921 1982 (Exhibit 211).
Beutler et al., Control of cachectin (tumor necrosis factor) synthesis: mechanisms of endotoxin resistance. *Science* vol. 232 pp. 977-980 1986 (Exhibit 212).
Biener-Ramanujan et al., Functional signaling of membrane-bound TL1A induces IFN-gamma expression. *FEBS Lett* vol. 11 pp. 2376-2380 2010 (Exhibit 213).
Bioque et al., Further evidence for a genetic association of interleukin-1 receptor antagonist and ulcerative colitis in the Northern and Mediterranean population. Abstract only *Gastroenterology* XP00673121 vol. 108 p. a783 1995 (Exhibit 214).
Boirivant et al., Hypoproliferative human lamina propia T cells retain the capacity to secrete lymphokines when stimulated via CD2/CD28 pathways. *Proceedings of the association of American physicians* Abstract Only *Proc Assoc Am Physicians* vol. 108 pp. 55-67 1996 (Exhibit 215).
Bourinbaiar et al., Pregnancy hormones, estrogen and progesteron prevent HIV-1 synthesis in monocytes but not in lymphocytes. *FEBS Letters* vol. 302 pp. 206-208 1992 (Exhibit 216).
Brabin L., Interactions of the female hormonal environment, susceptibility to viral infection and disease progression. *AIDS Patient Care and STDs.* vol. 16, pp. 211-221 2002 (Exhibit 217).
Braegger et al., Tumor necrosis factor alpha in stool as a marker of intestinal inflammation. *The Lancet* vol. 339 pp. 89-91 1992 (Exhibit 218).
Brambs et al., Inflammatory Bowel Disease: Radiographical diagnostics. (reprints available at the Department of Radiography, Albert Ludwigs University Hospital, Freiburg, Federal Republic of Germany, pp. 3-62 undated (Exhibit 219).
Brant et al., American families with Crohn's disease have strong evidence for linkage to chromosomes 16 but not chromosome 12. *Gastroentrol* vol. 115 pp. 1056-1061 1998 (Exhibit 220).
Braun et al., Chapter 13: Multiparameter analysis of immunogenetic mechanisms in clinical diagnosis and mamagement of inflammatory bowel disease. *Immune mechanisms in inflammatory bowel disease* edited by Richard S. Blumberg and Markus F. Neurath Mar. 10, 2006, Springer first edition pp. 209-218 (Exhibit 221).

Bream et al., A single nucleotide polymorphism in the proximal IFN-gamma promoter alters control of gene transcription. *Genes and Immunity* vol. 3 pp. 165-169 2002 (Exhibit 222).

Buning et al., Heterozygosity for IL23R, p.Arg318Gln confers a protective effect not only against Crohn's disease but also ulcerative colitis. *Aliment. Pharmacol Ther.* vol. 26 pp. 1025-1033 2007 (Exhibit 223).

Burks, C et al., GenBank *Nucleic Acids Res (Suppl)* vol. 29 pp. 2065-2069 1992 (Exhibit 224).

Bush et al., Cancer chemoresistance: the relationship between p53 and multidrug transporters *Int J Cancer* vol. 98 pp. 323-330 2002 (Exhibit 225).

Calemine, J. B. et al. Immunomodulation by diethylstillbestrol is dose and gender related: effects on thymocyte apoptosis and mitogen-induced proliferation. *Toxicology* vol. 178 pp. 101-118 2002 (Exhibit 226).

Cardullo et al., Detection of nucleic acid hybridization by nonradiative fluorescence resonance energy transfer. *Proc Natl Acad Sci. USA* vol. 85 pp. 8790-8794 1992 (Exhibit 227).

Casini-Raggi et al., Mucosal imbalance of IL-1 and IL-1 receptor antagonist in inflammatory bowel disease. *J Immunol* vol. 154 pp. 2434-2440 1995 (Exhibit 228).

Cavanaugh et al., Analysis of Australian Crohn's disease pedigrees refines the localization for susceptibility to inflammatory bowel disease on chromosome 16. *Ann Hum Genet* vol. 62 pp. 291-298 1998 (Exhibit 229).

Cenci et al., Estrogen deficiency induces bone loss by increasing T cell proliferation and lifespan through IFN-gamma induced class II transactivator. *Proc Natl Acad Sci.* vol. 100 pp. 10405-10410 2003 (Exhibit 230).

Chaudhary et al., Prediction of response to infliximab in Crohn's disease. *Digestive and Liver Disease* vol. 37 pp. 559-563 2005 (Exhibit 231).

Chevillard et al. Two new polymorphisms in the human interferon gamma promoter. *Eur J Immunogenetics* vol. 29 pp. 52-56 2002 (Exhibit 232).

Chiaretti, S et al., Gene expression profile of adult T-cell acute lymphocytic leukemia identifies distinct subsets of patients with different responses to therapy and survival. *Blood* vol. 103 pp. 2771-2778 2004 (Exhibit 233).

Cho et al., Confirmation of a susceptibility locus for Crohn's disease on chromosome 16. *Inflamm Bowel Dis.* vol. 3 pp. 186-190 1997 (Exhibit 234).

Cho et al., Identification of novel susceptibility loci for inflammatory bowel disease on chromosome 1p, 3q and 4q: evidence for epistasis between 1p and 1BD1. *Proc Natl Acad Sci* vol. 95 pp. 7501-7501 1998 (Exhibit 235).

Cippitelli et al. Retinoic acid-induced transcriptional modulation of the human interferon-gamma promoter. *J Biol Chemistry* vol. 271 pp. 26783-26793 1996 (Exhibit 236).

Cippitelli et al., Vitamin D3: a trasncriptional modulator of the interferon-gamma gene. *Eur J Immunol* Abstract Only vol. 28 pp. 3017-3030 1998 (Exhibit 237).

Costello et al., Dissection of the inflammatory bowel disease transcriptome using genome wide cDNA microarrays. *PloS Medicine* vol. 2 pp. 0771-0787 2005 (Exhibit 238).

Curran et al., Genetic analysis of inflammatory bowel disease in a large European cohort supports linkage to chromosome 12 and 16. *Gastroenterology* vol. 115 pp. 1066-1071 1998 (Exhibit 239).

Cushman et al., Effects of estrogen and selective estrogen receptor modulators in hemostasis and inflammation: potential differences among drugs. *Annals of New York Academy of Sciences* Abstract Only vol. 949 pp. 175-180 2001 (Exhibit 240).

Cushman et al., Tamoxifen and cardiac risk factors in healthy women—suggestion of an anti-inflammatory effect, arteriosclerosis, thrombosis and vascular biology. *Arterioscler Thromb Vasc Biol* vol. 21 pp. 251-266 2001 (Exhibit 241).

Cuzzocrea et al., 19beta-estradiol anti-inflammatory activitiy in Carrageenan-induced pleurisy. *Endocrinology* vol. 141 pp. 1455-1465 2000 (Exhibit 242).

Derrkx et al., Tumor-necrosis-factor antibody treatment in Crohn's disease. *The Lancet* vol. 342 pp. 173-174 1993 (Exhibit 243).

DeSilva et al., Pharmacogenetics of infliximab in Crohn's disease: the 5q31/IBD5 risk haplotype predict response. *Gastroenterology* 2002 vol. 122 Abstract M1423 (Exhibit 244).

Devlin et al., NOD2 variants and antibody response to microbial antigens in Crohn's disease patients and their unaffected relatives. *Gastroenterology* vol. 132 pp. 576-586 2007 (Exhibit 245).

Devlin et al., NOD2 variants are significantly associated with sero-reactivity to microbial antigens in Crohn's disease. Abstract Only 2006 Journal unknown (Exhibit 246).

Devlin et al., The p631H variant of the TLR2 gene associated with sero-reactivity to microbial antigens in Jewish patients with Crohn's disease. Abstract Only 2007 Journal unknown (Exhibit 247).

Diamond, M. S. et al., Binding of the integrin Mac-1 (CD11b/CD18) to the third immunoglobulin-like domain of ICAM01 (CD54) and its regulation by glycosylation. *Cell* vol. 65 pp. 961-971 1991 (Exhibit 248).

Diamond, M. S. et al., ICAM-1 (CD54): A counter receptor for Mac-1 (CD11b/CD18). *J Cell Biol* vol. 111 pp. 3129-3139 1990 (Exhibit 249).

Dib et al., A comprehensive genetic map of the human based on 5,264 microsatellites. *Nature* vol. 380 pp. 152-154 1996 (Exhibit 250).

Dubinsky et al., CARD8: A novel association with childhood onset ulcerative colitis (UC). *AGA Institute* Abstract # T1983 p. A-587 2006 (Exhibit 251).

Dubinsky et al., Familial expression of serological immune responses in pediatric IBD. *J of Pediatric Gastroenterology and Nutrition* Abstract #150 vol. 41 p. 539 2005 (Exhibit 252).

Dubinsky et al., IL-23 receptor (IL-23R) gene protects against pediatric Crohn's disease. *Inflamm Bowel Disease* vol. 13 pp. 511-515 2007 (Exhibit 253).

Dubinsky et al., Increased immune reactivity predicts aggressive complicating Crohn's disease in children. Abstract only 2007 Journal unknown (Exhibit 254).

Dubinsky et al., Serum immune responses predict rapid disease progression among children with Chron's disease: immune responses predict disease progression. *Am J. Gastroenterology* vol. 101 pp. 360-367 2006 (Exhibit 255).

Duerr R. H. et al., A genome-wide association study identifies IL23R as an inflammatory bowel disease gene. *Science Express* vol. 314 pp. 1-5 2006 (Exhibit 256).

Duerr R. H. et al., Association between ulcerative colitis and a polymorphism in intron 2 of the interleukin-2 receptor antagonist gene. *Gastroenterology* Abstract Only vol. 108 p. a812 1995 (Exhibit 257).

Duerr R. H. et al., Homozygosity for an HLA class II group haplotype is associated with pANCA positive and familial ulcerative colitis. Abstract only *Gastroenterology* vol. 108 p. a812 1995 (Exhibit 258).

Duerr R. H. et al., Linkage and association between inflammatory bowel disease and a locus on chromosom 12. *Am J Hum Genet* vol. 63 pp. 95-100 1998 (Exhibit 259).

Email from James Jenkins referencing the "Amazon.com" website regarding exact publication date of "Immune Mechanism in Inflammatroy Bowel Disease", edited by Richard S. Blumberg and Markus F. Neurath; Springer first edition. Received Dec. 15, 2010, 2 pages (Exhibit 260).

Erlandsson et al., Effects of raloxifene, a selective estrogen receptor modulator on thymus T cell reactivity and inflammation in mice. *Cellular Immunology* vol. 205 pp. 103-109 2000 (Exhibit 261).

Erlich et al., Chapter 32 HLA DNA typing. PCR protocols. Edited by Innis et al. pp. 261-271 (Exhibit 262).

Ewens and Spielman, The transmission/disequilibrium test: history, subdivision, and admixture. *Am J Hum Genetics* vol. 57 pp. 455-464 1995 (Exhibit 263).

Fawcett, J. et al., Molecular cloning of ICAM-3, a third ligand for LFA-1, constitutively expressed on resting leukocytes. *Nature* vol. 360 1992 (Exhibit 264).

Feder et al., A novel MHC class I-like gene is mutated in patients with hereditary heaemochromatosis. *Nature Genetics* vol. 13 pp. 399-408 1996 (Exhibit 265).

Ferrante et al., Predictors of early response to infliximab in patients with ulcerative colitis. *Inflamm Bowel Disease* 2007 vol. 13 pp. 123-128 (Exhibit 266).

Ferraris et al., Analysis of CARD15 gene variants in Italian pediatric patients with inflammatory bowel disease. *J of Pediatrics* pp. 272-273 2005 (Exhibit 267).

Fleshner et al., Both preoperative pANCA and CBir1 flagellin expression in ulcerative colitis (UC) patients influence pouchitis developemt after illeal pouch-anal anastomosis (IPAA). Abstract only 2006 (Exhibit 268), Gastroenterology 130(4) : A25.

Flores Mona G. et al. In vitro evaluation of the effects of candidate immunosuppressive drugs: flow cytometry and quantitative real-time PCR as two independent and correlated read-outs. *Journal of Immunological Methods* vol. 289 pp. 123-135 2004 (Exhibit 269).

Fox et al., Estrogen regulates the IFN-gamma promoter. *J Immunol* vol. 146 pp. 4362-4367 1991 (Exhibit 270).

Fujikado et al., Identification of arthritis related gene clusters by microarray analysis analysis of two independent mouse models for rheumatoid arthritis. *Arthritis Research and Therapy* vol. 8 pp. 1-13 2006 (Exhibit 271).

Fujino et al., Increased expression of interleukin 17 in inflammatory bowel disease gene. *Gut* vol. 52 pp. 65-70 2003 (Exhibit 272).

Garcia-Bates et al., Peroxisome proliferator-activated receptor gamma ligands enhance human B cell antibody production and differentiation. *J Immunology* vol. 183 pp. 6903-6912 2009 (Exhibit 273).

Gasche et al., A simple classification of Crohn's disease: report of the working party for the world congresses of gastroenterology, Vienna. *Inflammatory Bowel Disease* vol. 6 pp. 8-15 2000 (Exhibit 274).

Gewirtz et al., Dominant-negative TLR5 polymorphism reduces adaptive immune response to flagellin and negatively associates with Crohn's disease. *Am J Physiol Gastrointest Liver Physiol* 290: pp. G1157-G1163, 2006 (Exhibit 286).

Ghosh et al., Anti-TNF therapy in Crohn's disease *Novartis Foundation Symposium* vol. 263 pp. 193-218 2004 (Exhibit 287).

Giacomelli et al., Combination therapy with cyclosporin and methotrexate in patients with early rheumatoid arthritis soon inhibits TNF production without decreasing TNF mRNA level: an in vivo and in vitro study. *Clinical and Experimental Rheumatology* vol. 20 pp. 365-372 2002 (Exhibit 288).

Gilmore et al., Effect of estradiol on cytokine secretion by proteolipid proten-specific T cell clones isolated from multiple sclerosis patients and normal control subjects. *J Immmunology* Abstract only vol. 158 pp. 446-451 1997 (Exhibit 289).

Gonsky et al., CD2 mediates activation of the IGN-gamma intronic STAT binding region in mucosal T cells. *Eur J Immunol* vol. 33 pp. 1152-1162 2003 (Exhibit 290).

Gonsky et al., Mucosa-specific targets for regulation of IFN-gamma expression: lamia propia T cells use different cis-elements than peripheral blood T cells to regulate transactivation of IFN-gamma expression. *J Immunol* vol. 164 pp. 1399-1407 2000 (Exhibit 291).

Greenstein et al., Perforating and non-perforating indications for repeated operation in Crohn's disease: evidence of two clinical forms. *Gut* vol. 29 pp. 588-592 1988 (Exhibit 292).

Haertel C. et al., Dose-dependent immunomodulatory effects of acetylsalicylic acid and indomethacin in human whole blood: potential role of cyclooxygenase-2 inhibition. *Scandanavian Journal Immunology* vol. 60 pp. 412-420 2004 (Exhibit 293).

Hampe et al., A genomewide analysis provides evidence for novel linkage in inflammatory bowel disease in a large European cohort. *Am J Hum Genet* vol. 64 pp. 808-816 1999 (Exhibit 294).

Hampe et al., A genome-wide association scan of nonsynonymous SNPs identifies a susceptibility variant for Crohn disease in ATG16L1 *Nature Genetics* vol. 39 pp. 207-211 2007 (Exhibit 295).

Hampe et al., Association between insertion mutation in NOD2 gene and Crohn's disease in German and British populations. *Lancet* vol. 357 pp. 1925-1928 2001 (Exhibit 296).

Hampe et al., Association of NOD2 (CARD15) genotype with clinical course of Crohn's disease: a cohort study. *Lancet* Lancet Limited pp. 1661-1665 vol. 35 2002 (Exhibit 297).

Hanifi et al., Genetic structure of IDDM1: two separate regions in the major histocompatibility complex contribute to suceptibility or protection. *Diabetes A Journal of the American Diabetes Association* vol. 47 pp. 1-7 1999 (Exhibit 298).

Harnish et al. Beneficial effects of estrogen treatment in the HLA-B27 trangenic rat model of inflammatory bowel disease. *Am J Physiol Gastrointest Liver Physiology* vol. 286 pp. G118-124 2004 (Exhibit 299).

Hartel, Christopher et al., Delayed cytokine mRNA expresion kinetics after T-lymphocyte costimulation: A quantitative measure of the efficacy of cyclosporin A-based immunosuppression. *Clinical Chemistry* vol. 48 pp. 2225-2231 2002 (Exhibit 300).

Hazra et al., Common variant of FUT2 are associated with plasma vitamin B12 levels. *Nature Genetics* vol. 40 pp. 1160-1162 2008 (Exhibit 301).

Herbon et al. High-resolution SNP scan of chromosome 6p21 in pooled samples from patients with complex diseases. *Genomics* vol. 81 pp. 510-518 2003 (Exhibit 302).

Heresbach et al., NOD2/CARD15 gene polymorphisms in Crohn's disease: a genotype-phenotype analysis. *Eur J Gastroenterology and Hepatology* vol. 16 pp. 55-62 2004 (Exhibit 303).

Hess et al., The hydroxylamine of sulfamethoxazole synergizeswith FK506 and cyclosporin A inhibiting T-cell proliferation *Journal of Pharmacology and Experimental Techniques* vol. 281 pp. 540-548 1996 (Exhibit 304).

Hirschhorn et al., A comprehensive review of genetic association studies. *Genetics in Medicine* vol. 4 pp. 45-61 2002 (Exhibit 305).

Hlavaty et al., Polymorphisms in apoptosis genes predict response to infliximab therapy in luminal and fistulizing Crohn's disease. *Aliment Pharmacol Ther* vol. 22 pp. 613-626 2005 (Exhibit 306).

Hogg, N. and Landis, R. Adhesion molecules in cell interactions. *Curr Opin Immunol.* vol. 5, pp. 383-390 1993 (Exhibit 307).

Hugot et al., Association of Nod2 leucine-rich repeat variants with sesceptibility to Crohn's disease. *Nature* vol. 411 pp. 599-603 2001 (Exhibit 310).

Hugot et al., Linkage analyses of chromosome 6 loci, including HLA, in familian aggregations of Crohn's disease GETAID. *Am J Med Genet* vol. 52 pp. 207-213 1994 (Exhibit 311).

Hugot et al., Mapping of a susceptibility locus for Crohn's disease on chromosome 16. *Nature* vol. 379 pp. 821-823 1996. (Exhibit 312).

Inohara et al., Human NOD1 confers responsiveness to bacterial lipopolysaccharides. *J Biol Chem* vol. 276 pp. 2551-2554 2001 (Exhibit 313).

Ioannidis et al., Replication validity of genetic association studies. *Nature Genetics* vol. 29 pp. 306-309 2001 (Exhibit 314).

Ippoliti et al., Combination of innate and adaptive immune alterations increased the liklihood of fibrostenosis in Crohn's disease. *Inflamm Bowel Disease* vol. 16 pp. 1279-1285 2010 (Exhibit 315).

Ippoliti et al., The relationship between abnormal innate and adaptive immune function and fibrostenosis in Crohn's disease patients. Abstract only. 2006 Journal unknown (Exhibit 316).

Iris et al., Dense Alu clustering and a potential new member of the NFkB family within a 90 kilobase HLA Class III segment *Nature Genetics* vol. 3 pp. 137-145 1993 (Exhibit 317).

Jacob et al., Definition of microsatellite size variants for Tnfa and Hsp70 in autoimmune and nonautoimmune mouse strains *Immunogenetics* vol. 36 pp. 182-188 1992 (Exhibit 318).

Jarjour et al., The 8.5 kb Patl allele of the stress protein gene Map70-2—an independent risk factor for systemic lupus erythematosus in African Americans. *Hum Immunol* vol. 45 pp. 59-63 1996 (Exhibit 319).

Johnston, M. I. et al. Present status and future prospects for HIV therapies. *Science* vol. 260 pp. 1286-1293 1993 (Exhibit 320).

Jongeneel et al., Extensive genetic polymorphism in the human tumor necrosis factor region and relation to extended HLA haplotypes. *Proc Natl Acad Sci* vol. 88 pp. 9717-9721 1991 (Exhibit 321).

Juhasz et al., Quantification of chemotherapeutic target gene mRNA expression in human breast cancer biopsies: comparison of real-time reverse transcription-PCR vs. relative quantification reverse transcription-PCR utilizing DNA sequence analysis of PCR product. *Journal of Clinical Laboratory Analysis* vol. 17 pp. 184-194 2003 (Exhibit 322).

Karpuzoglu-Sahin et al., Effects of long-term estrogen treatment on IFN-gamma, IL-2 and IL-4 gene expression and protein synthesis in spleen and thymus of normal C57BL/6 mice. *Cytokine* vol. 14 pp. 208-217 2001(Exhibit 323).

Karpuzoglu-Sahin et al., Interferon-gamma levels are upregulated by 17-beta-estradiol and diethylstibestrol. *J Reproductive Immunology* vol. 52 pp. 113-127 2001 (Exhibit 324).

Kim et al. DQCAR113and DQCAR115 in combination with HLA-DRB1 alleles are significant markers of susceptibility to rheumatoid artiritis in the Korean population. *Tissue Antigens* vol. 54 pp. 552-559 1999 (Exhibit 325).

Kirchhausen et al., Location of the domains of ICAM-1 by immunolabeling and single-molecule electron microscopy. *J Leukocyte Biology* vol. 53 pp. 342-346 1993 (Exhibit 326).

Kita, Y. et al., Sequence and expression of rat ICAM-1. *Biochim Biophys Acta* vol. 1131 pp. 108-111 1992 (Exhibit 327).

Klein N J et al., Ex-vivo assessment of candidate anti-inflammatory agents in the treatment of Gram-negative sepsis. *Immunology and Infectious Disease* vol. 4 pp. 33-35 1994 (Exhibit 328).

Koutroubakis et al., Tumor necrosis factor-alpha polymorphism in inflammatory bowel disease *Hellenic J of Gastroenterology* vol. 8 pp. 132-135 1995 (Exhibit 329).

Kugathansan et al., L1007FsinsC variant of CARD15/NOD2 is strongly associated with early onset and fibrostenosing behavior in pediatric Crohn's disease. *Gasteroenterology* vol. 126 No. 4 Supp 2 pp. A68 524 (Exhibit 330).

Kugathansan et al., Loci on 20q13 and 21q22 are associated with pediatric onset inflammatory bowel disease. *Nature Genetics* 2008 vol. 40 pp. 1211-1215 (Exhibit 331).

Kuntz, H. D. et al., Inflammatory Bowel Disease: endoscopic diagnostics. (Reprints available at the Department of Gastroenterology and Hepatology "Bergmannshell" Hospital, University of Bochum, Federal Republic of Germany) pp. 3-38 (Undated) (Exhibit 332).

Kutyavin et al., 3-minor groove binder-DNA probes increase sequence specificity at PCR extension temperatures. *Nucleic Acid Res* vol. 28 pp. 655-661 2000 (Exhibit 333).

Kutyavin et al., Oligonucleotides with conjugated dihyropyrroloindole tripeptides: base composition and backbone effects on hybridization. *Nucleic Acid Res* vol. 25 pp. 3718-3723 1997 (Exhibit 334).

Lakatos et al., NOD2/CARD15 mutations and genotype-phenotype correlations in patients with Crohn's disease. Hungarian multicenter study *Orv. Hetil.* vol. 145 pp. 1403-1411 2004 (Exhibit 335).

Landegren, U. et al., A ligase-mediated gene detection technique. *Science* vol. 241 pp. 1077-1080 1988 (Exhibit 336).

Lasky, L., Selectins: interpreters of cell-specific carbohydrate information during inflammation. *Science* vol. 258 pp. 964-969 1992 (Exhibit 337).

Latham et al., Estradiol treatment redirects the isotype of the autoantibody response and prevents the development of autoimmune arthritis. *J of Immunol* vol. 171 pp. 5820-5826 2003 (Exhibit 338).

Laurence et al. Effect of tamoxifen on regulation of viral replication and human immunodeficiency virus (HIV) long terminal repeat-directed transcription in cells chronically infected with HIV-1. *Blood* vol. 75 pp. 696-703 1990 (Exhibit 339).

Lee et al., Estrogen-mediated protection against HIV Tat protein-induced inflammatory pathways in human vascular endothelial cells. *Cardiovascular Research* vol. 63 pp. 139-148 2004 (Exhibit 340).

Lemna, W. K. et al., Mutation analysis for heterozygote detection and the prenatal diagnosis of cystic firbosis. *N. Eng. J. Med.* vol. 322 pp. 291-296 1990 (Exhibit 341).

Leong et al., NOD2/CARD15 gene polymorphisms and Crohn's disease in the Chinese population. *Aliment Pharmacol Thera* vol. 17 pp. 1465-1470 2003 (Exhibit 342).

Lesage et al., CARD15/NOD2 mutational analysis and genotype-phenotype correlation in 612 patients with inflammatory bowel disease. *Am J of Human Genetics* vol. 70 pp. 845-857 2002 (Exhibit 343).

Leung, S. Y. et al. Expression profiling identifies chemokine (C-C Motif) ligand 18 as an independent prognostic indicator of gastric cancer. *Gastroenterology* vol. 127 pp. 457-469 2004 (Exhibit 344).

Li et al., Cloning, characterization and the complete 56.8-kilobase DNA sequence of the human NOTCH4 gene. *Genomics* vol. 51 pp. 45-58 1998 (Exhibit 345).

Li et al., New serological biomarkers of inflammatory bowel disease. *World J of Gastroenterology* vol. 14 pp. 5115-5125 2008 (Exhibit 346).

Limbergen et al., IL23R Arg381 Gln is associated with childhood onset inflammatory bowel disease in Scotland. *Gut* vol. 56 pp. 1173-1174 2007 (Exhibit 347).

Linder et al. Tamoxifen enhances interferon regulated gene expression in breat cancel cells. *Molecular and Cellular Biochemistry* Abstract Only vol. 167 pp. 169-177 1997 (Exhibit 348).

Lipsky, P. Structure, function and regulation of molecules involved in leukocyte adhesion. New York: Springer-Verlag 1993 Book not included.

Liu et al., Mucosal gene expression profiles following the colonization of immunocompetent defined-flora C3H mice wih *Helicobacter bilis*: a prelude to typhlocolitis. *Microbes and Infection* vol. 11 pp. 374-383 2009 (Exhibit 350).

Livak, Allelic discrimination using fluorogenic probes and the 5' nuclease assay. *Genetic Analysis* vol. 14 pp. 143-149 1999 (Exhibit 351).

Lodes et al., Bacterial flagellin is a dominant antigen in Crohn disease. *Journal of Clinical Investigation*, vol. 113, pp. 1296-1306 May 2004 (Exhibit 352).

Lorenz-Meyer, H. Inflammatory Bowel Disease Laboratory Diagnostics. (Reprints available from the City Hospital, Friedrichshafen, Federal Republic of Germany) pp. 3-29 (undated) (Exhibit 353).

Louis et al., Association between polymorphism in IgG Fc receptor IIIa coding gene and biological response to infliximab in Crohn's disease. *Aliment Pharmacol Ther* 2004 vol. 19 pp. 511-519 (Exhibit 354).

Macdonald et al., Tumor necrosis factor-alpha and interferon-gamma production measured at the single cell level in normal and inflamed human intestine *Clin Exp Immunol* vol. 81 pp. 301-302 1990 (Exhibit 355).

Maniatis, T. et al. Molecular Cloning: A laboratory manual. Cold Spring Harbor Laboratory press. 1982 Book not included.

Mansfield et al., Novel genetic association between ulcerative colitis and the antiinflammatory cytokine interleukin-1 receptor antagonist. *Gastroenterology* pp. 637-642 vol. 106 1994 (Exhibit 357).

Martin et al., Recombination rates across the HLA complex: use of microsatellites as a rapid screen for recombinant chromosome. *Human Molecular Genetics* vol. 4 pp. 423-428 1995 (Exhibit 358).

Martins et al., Transcriptional repressor Blimp-1 regulates T cell homeostasis and function. *Nature Immunology* vol. 7, pp. 457-265 2006 (Exhibit 359).

Mascheretti et al. Pharmacogenetic investigation of the TNF/TNF-receptor system in patients with chronic active Crohn's disease treated with infliximib *The Pharmacogenomics Journal* vol. 2 pp. 127-136 2002 (Exhibit 360).

Matalka, K. Z. The effect of estradiol but not progesterone on the production of cytokines in stimulated whole blood is concentration-dependent. *Neuro Endocrinology Letters* Abstract only. vol. 24 pp. 185-191 2003 (Exhibit 361).

Matejuk et al., 17-beta-estradiol inhibits cytokine, chemokine and chemokine receptor mRNA expression in the central nervous system of gemale mice with experimental autoimmune encephalomyelitis. *J of Neuroscience Research* vol. 65 pp. 529-542 2001 (Exhibit 362).

Matsunaga, Hiroko et al., Application of differential displayto identify genes fir lung cancer detection in peripheral blood. *Int J of Cancer* vol. 100 pp. 593-599 2002 (Exhibit 363).

McCall et al., Constitutive expression of TNF-a and of an IL-8 gene is associated with genetic susceptibility to chronic granulomatous enterocolitis in inbred rats *AGA Abstracts* p. A740 1993 (Exhibit 364).

McEver, R. Leukocyte—endothelial cell interactions. *Curr Opin Cell Biol* vol. 4 pp. 840-849 1992 (Exhibit 365).

Mehmut et al., Fas ligand and TNF-related apoptosis-inducing ligand induction of infiltrating lymphocytes in bladder carcinoma by Bacillus Calmette-Guerin treatment *Urologica International* vol. 75 pp. 87-88 2005 (Exhibit 366).

Mei et al., Familial expression of anti-*Escherichia coli* outer membrane porin C in relatives of patients with Crohn's disease. *Gastroenterology* vol. 130 pp. 1078-1085 2006 (Exhibit 367).

Mei L., Association between IL17A and IL17RA genes and inflammatory bowel disease (IBD). Abstract only 2007 Journal unknown (Exhibit 368).

Melmed et al., A prospective analysis of predictive factors for the diagnosis of Crohn's disease after Ileal pouch-anal anastomosis for ulcerative colitis. Abstract only 2007 Journal unknown (Exhibit 369).

Melmed et al., Patients with inflammatry bowel disease are at risk for vaccine-preventable illness. *Am J Gasteroenterol* vol. 101 pp. 1834-1849 2006 (Exhibit 370).

Mesange et al., Ligands of the antiestrogen-binding site are able to inhibit virion production of human immunodeficiency virus 1-infected lymphocytes. *Molecular Pharmacology* vol. 50 pp. 75-79 1996 Abstract only (Exhibit 371).

Messer et al., Polymorphic structure of the tumor necrosis factor (TNF) locus: an NcoI polymorphism in the first intron of TNF-B gene correlates with a variant in amino acid position 26 and a reduced level of TNF-B production *J Exp Med* vol. 173 pp. 209-219 1991 (Exhibit 372).

Milner and Campbell. Polymorphic analysis of the three MHC-linked HSP70 genes. *Immunogenetics* vol. 36 pp. 357-362 1992 (Exhibit 373).

Mingjia et al., How oestrogen or progesterone might change a woman's susceptibility to HIV-1 infections. *The Australian and New Zealand Journal of Obstetrics and Gynecology* Abstract only. vol. 42 pp. 472-475 2002 (Exhibit 374).

Misiewicz et al., The estrogen antagonist tamoxifen inhibits carrageenan induced inflammation in LEW/N female rats. *Life Sciences* vol. 58 pp. PL281-286 1996 (Exhibit 375).

Moghaddam et al., Genetic structure of IDDM1: two separate regions in the major histocompatibility complex contribute to susceptibility or protection. *Diabetes* vol. 47 pp. 263-269 1998 (Exhibit 376).

Mow et al., Association of antibody responses to microbial antigens and complications of small bowel Crohn's disease. *Gastroenterology* vol. 126 pp. 414-424 2004 (Exhibit 377).

Murch et al., Location of tumor necrosis factor alpha by immunochemistry in chronic inflammatory bowel disease *Gut* vol. 34 pp. 1705-1709 1993 (Exhibit 378).

Murillo et al., CARD15 gene and the classification of Crohn's disease. *Immunogenetics* vol. 54 pp. 59-61 2002 (Exhibit 379).

Murray et al., GenBank Accession No. G08322, Feb. 5, 1997 (Exhibit 380).

Nadal et al., Imbalance in the composition of the duodenal microbiata of children with coeliac disease. *J Medical Microbiol* vol. 56 pp. 1669-1674 2007 (Exhibit 381).

Nakamura et al., In situ expression of the cell adhesion molecules in Inflammatory Bowel Disease; evidence of immunologic activation of vascular endothelial cells. *Lab. Investig.* vol. 69 No. 1, pp. 77-85, 1993 (Exhibit 382).

Nakaya et al., Estrogenic compounds suppressed interferon-gamma production in mouse splenocytes through direct cell-cell interaction. *In vitro cellular and developmental biology animal.* vol. 39 pp. 383-387 2003 (Exhibit 383).

Nedospasov et al., Genetic polymorphism of the human gene locus containing genes for tumor necrosis factors: ethnic differences in allele frequency distribution, Chemical Abstracts, vol. 120, No. 5, 1994, Columbus, Ohio, US, abstract No. 47183y. (Exhibit 398).

Nedospasov, S.A., et al., DNA sequence polymorphism at the human tumor necrosis factor (TNF) locus. Numerous TNF/lymphotoxin alleles tagged by two closely linked microsatellites in the upstream region of the lymphotoxin (TNF-beta) gene. *J. Immunol.* vol. 147 pp. 1053-1059 1991 (Exhibit 399).

Ogura et al., NOD2, a Nod1/Apaf-1 family member that is restricted to monocytes and activates NF-kB. *J Biol Chem* vol. 276 pp. 4812-4818 2001 (Exhibit 400).

Ogura, Y. et al., A frameshift mutation in NOD2 associates with susceotibility to Crohn's disease. *Nature* vol. 411: pp. 603-606, 2001 (Exhibit 401).

Ohmen et al., Susceptibility locus for inflammatory bowl disease on chromosome 16 has a tole in Crohn's disease, but not in ulcerative colitis. *Hum Mol Genet* vol. 5 pp. 1679-1683 1996 (Exhibit 402).

Okazaki et al., Contributions of the IBD5, IL23R, ATG16L1, and NOD2 to Crohn's disease risk in a population-based case-controlled study: evidence of gene-gene interaction *Inflamm Bowel Disease* vol. 14 pp. 1528-1541 2008 (Exhibit 403).

Orholm et al., Familial occurrence of inflammatory bowel disease. *New England Journal of Medicine* vol. 84 pp. 84-88 1991 (Exhibit 404).

Over et al., Thromphilia and inflammatroy bowel disease: does factor V mutation have a role? *European Journal of Gastroenterology and Hepatology* vol. 10 pp. 827-829 1998 (Exhibit 405).

Owerbach and Gabbay. The HOXD8 locus (2q31) is linked to type I diabetes—interaction with chromosome 6 and 11 disease susceptibility genes. *Diabetes* vol. 44 p. 132-136 1995 (Exhibit 406).

Papadakis et al., An interaction between IL-23R and IL-17A and between IL-23R and IL-17RA haplotypes is necessary for susceptibility to Crohn's disease. Abstract only 2007 Journal unknown (Exhibit 407).

Papadakis et al., Anti-Flagellin (Cbir1) phenotypic and genetic Crohn's Disease associations, *Inflamm Bowel Dis*, vol. 13, No. 5, May 2007 (Exhibit 408).

Papadakis et al., Phenotypic and functional characterization of CCR9+ T lymphocytes in small intestinal Crohn's disease. Abstract only. 2006 Journal unknown (Exhibit 409).

Papp et al., Seroreactivity to microbial components in Crohn's disease is associated with Ileal involvement, noninflammatory disease behavior and NOD2/CARD15 genotype but not with risk for surgery in a Hungarian cohort of IBD patients. *Inflamm Bowel Disease* vol. 13 pp. 984-992 2007 (Exhibit 410).

Parkes et al., Susceptibility loci in inflammatory bowel disease. *Lancet* vol. 348 p. 1588 1996 (Exhibit 411).

Parrello et al., Upregulation of the IL-12 receptor beta 2 chain in Crohn's disease. *J Immunol* vol. 165 pp. 7234-7239 2000 (Exhibit 412).

Partanen, J., et al., Low degree of DNA polymorphism in the HLA-linked lymphotoxin (tumor necrosis factor-B) gene. *Scand J. Immunol.* vol. 28 pp. 313-316 1988. (Exhibit 413).

Paul, ed. Fundamental Immunology 4th edition pages Chapter 19 663-665 1998 (Exhibit 414).

Pericak-Vance et al., Approaches to gene mapping in complex human diseases. Wiley-Liss New York 1998 (Exhibit 415).

Perkin Elmer Catalog 1992 p. 12 (Exhibit 416).

Plevy et al, Tumor necrosis factor (TFN) microsatellite associations with HLA-DR2+ patients define crohn's disease (cd) and ulcerative colitis (uc)-specific genotypes, *Gastroenterology*, vol. 106, p. A754 1994 (Exhibit 417).

Plevy et al. TNF-alpha MRNA levels differentiated mucosal inflammation in crohn's disease from ulcerative colitis, *J. Immunology*, vol. 150, p. 10a 1993 (Exhibit 418).

Plevy et al., A role of TNF-alpha and mucosal T-helper-1 cytokines in the pathogenesis of Crohn's disease. *The Journal of Immunology* vol. 84 pp. 1397-1398 2004 (Exhibit 419).

Plevy et al., Increased mucosal tnf-alpha mrna levels and numbers of tnf-alpha producing cells are unique to mucosal inflammation in crohn's disease, *Faseb Journal*, Abstract 5849 vol. 8, p. A1010 Apr. 1994, (Exhibit 420).

Plevy et al., The tumor necrosis factor (TNF) microsatellite haplotype A2B1C2D4E1 correlates with increased TNF production in Crohn's disease. Abstract only AASLD at Digestive disease week 1995 (Exhibit 421).

Plevy et al., Tumor necrosis factor microsatellites define Crohn's disease—associated haplotype on chromosome 6. *Gasteroenterology* vol. 110 pp. 1053-1060 1996 (Exhibit 422).

Pociot et al., Association of tumor necrosis factor and class II major histocompatibility complex alles with secretion of tnf alfa and tnf beta by human mononuclear cells: a possible link to insulin-dependent diabetes mellitus, 1993, Abstract only *Eur. J. Immunology*, vol. 23, 1993 (Exhibit 423).

Pociot, F., et al., "A tumor necrosis factor beta gene polymorphism in relation to monokine secretion and insulin dependent diabetes mellitus." *Scand J. Immunol.*, vol. 33 pp. 37-49 1991 (Exhibit 424).

Poicot et al., Polymorphic analyis of the human MHC-linked heat shock protein 70 (HSP70-2) and HSP70-Hom genes in insulin-dependent diabetes mellitus (IDDM). *Scand J Immunol* vol. 38 pp. 491-495 1993 (Exhibit 425).

Polanczyk et al., The protective effect of 17beta-estradiol on experimental autoimmune encephalomyelitis is mediated through estrogen receptor-a. *Americal J of Pathology* vol. 163 pp. 5820-5827 2003 (Exhibit 426).

Potts et al., Using micorbicides to fight the spread of HIV. *Science* vol. 300 p. 431 2003 (Exhibit 427).

Radlmayr, M. et al., The c-insertion mutation of the NOD2 gene is associated with fistulizing and fibrostenotic phenotypes in Crohn'd diseases. *Gastererology* vol. 122 pp. 2091-2095 2002 (Exhibit 428).

Rector et al., Mannan-binding lectin (MBL) gene polymorphisms in ulcerative colitis and Crohn's disease. *Genes and Immunity* vol. 2 pp. 323-328 2001 (Exhibit 429).

Reinecker et al., Enhanced secretion of tumor necrosis factor-alpha, IL-6 and IL-1beta by isolated lamina propia mononuclear cells from patients with ulcerative colitis and Crohn's disease *Clin Exp Immunol* vol. 94 pp. 174-181 1993 (Exhibit 430).

Rioux et al., Genome-wide association study identifies new susceptibility loci for Crohn disease and implicates autophagy in disease pathogenesis *Nature Genetics* pp. 1-9 2007 (Exhibit 431).

Rodriguez-Caballero et al., A new simple whole blood flow cytometry-based method for simultaneous identification of activated cells and quantitative evaluation of cytokines released during activation *Laboratory Investigation* vol. 84 pp. 1387-1398 2004 (Exhibit 432).

Roth et al., Familial empiric risk estimates of inflammatory bowel disease in Ashkenazi Jews. *Gastroenterology* vol. 96 pp. 1016-1020 1989 (Exhibit 433).

Roth et al., Geographic origins of Jewish patients with inflammatory bowel disease. *Gastroenterology* vol. 97. pp. 900-904 1989 (Exhibit 434).

Rotter et al., TLR5 polymorphisms are associated with OmpC and CBir1 expression and with severity of Crohn's disease in Ashkenazi Jews. Abstract only 2004. Journal unknown (Exhibit 435).

Rozen et al., Crohn's disease in the Jewish population of Tel-Aviv-Yafo: epidemiologic and clinical aspects. *Gastroenterology* vol. 76 pp. 25-30 1979 (Exhibit 436).

Salem et al., Mediation of the immunomodulatory effect of beta-estradiol on inflammatory response by inhibition of recruitment and activation of inflammatory cells and their gene expression of TNFf-alpha and IFN-gamma. *Intl Archives of Allergy and Immunology* Abstract Only. vol. 121 pp. 235-245 2000 (Exhibit 437).

Salem M. L. Estrogen, a double-edged sword: modulation of TH1- and THw- medicated inflammations by differential regualtion of TJ1/TH2 cytokine production. *Inflammation and Allergy* vol. 3 pp. 97-104 2004 (Exhibit 438).

Saruta et al., High frequency haplotypes in the X-chromosome locus TLR8 are associated with both CD and UC in females. 2007 Journal unknown (Exhibit 439).

Saruta et al., TLR8-mediated activation of human monocytes inhibits TL1A expression. *Eur J Immunol* vol. 39 pp. 2195-2202 2009 (Exhibit 440).

Sategna-Guidetti et al., Tumor necrosis factor/cachectin in Crohn's disease—relation of serum concentration to disease activity *Recenti Progressi*, vol. 84, pp. 93-99 1993 (Exhibit 441).

Satsangi et al., The genetics of inflammatory bowel disease. *Gut* vol. 40 pp. 572-574 1997 (Exhibit 442).

Saxon, E. Z. et al., A distinct subset of antineutrophil cytoplasmic antibodies is associated with inflammatory bowel disease. *J Allergy Clin. Immunol.* vol. 86 pp. 202-210 1990 (Exhibit 443).

Schimanski, C. C. et al., Efect of chemokine receptors CXCR4 and CCR7 on the metastatic behavior of human colorectal cancer *Clinical Cancer Research* vol. 11 pp. 1743-1750 2005 (Exhibit 444).

Schluender et al., Does infliximab influence surgical morbidity or long-term outcome of Ileal pouch-anal anastomosis in patients with ulcerative colitis. Abstract only 2006 Journal unknown (Exhibit 445).

Schluender et al., Does preoperative wireless endoscopic capsule predict long-term outcome after Ileal pouch-anal anastomosis (IPAA)? Abstract only 2006 Journal unknown (Exhibit 446).

Schoelmerich, J. Inflammatory Bowel Diseases: early symptoms and differential (Reprints available from University of Freiburg, Department of Internal Medicine, Hugstetter Strasse 55, D-7800 Freiburg, W. Germany) pp. 2-20 (Exhibit 447).

See, Darryl et al., Increased tumor necrosis factor alpha (TNF-alpha) and natural killer cell (NK) function using an integrative approach in late stage cancers. *Immunological Investigations* vol. 31 pp. 137-153 2002 (Exhibit 448).

Shanahan, F. et al., Inflammatory Bowel Disease. *Textbook of Internal Medicine* W.N. Kelley et al. (editor) 2nd edition J. B. Lippincott Company, Philadelphia vol. 81 pp. 489-502 1992 (Exhibit 449).

Shetty et al., Pharmacogenomics of response to anti-tumor necrosis factor therapy in patients with Crohn's disease. *American Journal of Pharmacogenomics* vol. 2 pp. 215-221 2202 (Exhibit 450).

Shovam et al., Evaluation of the BioPlex 2200 ANA screen: Analysis of 510 healthy subjects: incidence of natural/predictive autoantibodies. *Annals of the New York Academy of Science* vol. 1050 pp. 380-388 2005 (Exhibit 451).

Silman et al., Epidemiology and genetics of rheumatoid arthritis. *Arthritis Research* vol. 4 Supp 3 pp. S265-S272 2002 (Exhibit 452).

Silverberg et al., Evidence for linkage between Crohn's disease (CD) and a locus near the major histocompatibility complex (MHC) on chromosome 6 in a Canadian inflammatory bowel disease (IBD) population. *Gastroenterology* vol. 116:G3560 AGA Abstracts 1999 (Exhibit 453).

Silverberg et al., The HLA DRBL 0103 allele is associated with Crohn's disease (CD) in a Toronto inflammatory bowel disease (IBD) population. *Gastroenterology* vol. 116:G3559 AGA Abstracts 1999 (Exhibit 454).

Singal et al., D6S273 microsatellite polymorphism and susceptibility to Rhematoid Arthritis. *Tissue Antigens* vol. 52 pp. 353-358 1998 (Exhibit 455).

Singal et al., Genetics of rheumatoid arthritis (RA): two separate regions in the major histocompatibility complex contribute to susceptibility to RA. *Immunol Lett* vol. 69 pp. 301-306 1999 (Exhibit 456).

Sitaraman et al., Elevated flagellin-specific immunoglobulins in Crohn's disease. *Am J Physiol Gastrointest Liver Physiol* 288:G403-G406, 2005 (Exhibit 457).

Smith C. et al., Cooperative interactions of LFA-1 and Mac-1 with intercellular adhesion molecule-1 in facilitating adherence and transendothelial migration of human neurophils in vitro. *J Clin Invest* vol. 83 pp. 2008-2017 1998 (Exhibit 458).

Smith et al. Topical estrogen protects against SIV vaginal transmission without evidence of systemic effect. Abstract only. vol. 18 pp. 1637-1643 2004 (Exhibit 459).

Smith et al., Estrogen protects against vaginal transmission of simian immunodeficiency virus. *J Infectious Diseases* vol. 182 pp. 708-715 2000 (Exhibit 460).

Smith, C. W. et al., Recognition of an endothelial determinant for CD18-dependent human neutrophil adherence and transendothelial migration. *J Clin Invest* vol. 82 pp. 1746-1756 1988 (Exhibit 461).

Smith, C., Adherence of neutrophils to canine cardiac myocyyes in vitro is dependent on intercellular adhesion molecule-1. *J Clin Invest* vol. 88 pp. 1216-1223 1991 (Exhibit 462).

Smith, C., Transendothelial Migration, Harlan, J. and Liu D., eds., W. H. Freeman & Co. New York pp. 83-115 1992 (Exhibit 463).

Springer, T. A. et al., Adhesion receptors of the immune system. *Nature* vol. 346 pp. 425-433 1990 (Exhibit 464).

Springer, T. A. et al., Leukocyte adhesion molecules structure function and regulation. New York, Springer-Verlag 1990 Book-Table of Contents Book not included.

Staunton et al. The arrangement of the immunoglobulin-like domains of ICAM-1and binding sites for LFA-1 and rhinovirus. *Cell* vol. 61 pp. 243-254 1990 (Exhibit 466).

Staunton et al., Primary Structure of ICAM-1 demonstrates interaction between member of the immunoglobulin and integring supergene families. *Cell* vol. 52 pp. 925-933 Mar. 25, 1988 (Exhibit 467).

Steer et al., Development of rheumatoid arthritis is not associated with two polymorphisms in the Crohn's disease gene CARD15 *Rheumatology* vol. 42 pp. 304-307 2003 (Exhibit 468).

Stites, D. P., et al., Chapter 22 of the 4th edition of Basic and Clinical Immunology, Lange Medical Publications, Los Altos, California 1982 (Exhibit 469).

Stratagene Catalog 1988 p. 39 (Exhibit 470).

Strater, J. et al., Expression of TRAIL and TRAIL receptors in colon carcinoma: TRAIL-R1 is an independent prognostic parameter. *Clinical Cancer Research* vol. 8 pp. 3734-3740 2002 (Exhibit 471).

Stulik et al., The different expression of proteins recognized by monoclonal anti-heat shock protein 70 (hsp70) antibody in human colonic diseases. *Electrophoresis* vol. 18 pp. 625-628 1997 (Exhibit 472).

Su, X., Different haplotypes of IL12B (p40) genes are associated with clinical Crohn's disease (CD) and with CD patients expressing Cbir1 antibodies, respectively. Abstract only 2007 Journal unknown (Exhibit 473).

Sugaya et al., Gene organization of human NOTCH4 and (CTG)n polymorphism in this human counterpart gene of mouse proto-oncogene Int3. *Gene* vol. 189 pp. 235-244 1997 (Exhibit 474).

Sugaya et al., Three genes in the human MHC class III region near the junction with the class II: gene for receptor of advanced glycosylation end products, PBX2 homeobox gene and a notch homolog, human counterpart of mouse mammary tumor gene int-3. *Genomics* vol. 23 pp. 408-419 1994 (Exhibit 475).

Sullivan et al., Prevalence of a mutation causing C2 deficiency in systemic lupus erythematosus. *J of Rhematology* vol. 21 pp. 1128-1133 1994 (Exhibit 476).

Takedatsu, H., Reduced nuclear factor (NF)-kB expression in cell lines from anti-CBir1-associated NFKB1 haplotypes. Abstract only. 2007 Journal unknown (Exhibit 477).

Takedatsu et al., TL1A (TNFSF15) regulates the development of chronic colitis by modulating both T helper (TH)1 and TH17 activation. *Gastroenterology* vol. 135 pp. 552-567 2008 (Exhibit 478).

Targan et al., Antibodies to CBir1 flagellin define a unique response that is associated independently with complicated Crohn's disease. *Gastroenterology*, vol. 128, 2005, pp. 2020-20289 (Exhibit 479).

Targan et al., Definition of a lamina propia T cells responsive state enhanced cytokine responsiveness of T cells stimulated through the CD2 pathway. *J Immunol* vol. 154 pp. 664-675 1995 (Exhibit 480).

Targan, et al., Antibodies to a novel flagellin (CBir1) define a unique serologic response in Crohn's disease (CD). *Gastroenterology*, Abstract only XP009098183 vol. 126, No. 4, Suppl 2, Apr. 2004, p. A113 (Exhibit 481).

Tarlow J. K. et al., Polymorphism in human IL-1 receptor antagonist gene intron 2 is caused by variable numbers of an 86-bp tandem repeat. *Hum Genet* vol. 91 pp. 403-404 1993 (Exhibit 482).

Taylor et al., Analysis of IBD5-related polymorphisms: IRF1 but not SLC22A4 or SLC22A5 is associated with IBD in Puerto Rican populations. *Digestive Disease Week* Abstract only 2006 Journal unknown (Exhibit 483).

Taylor et al., Genes regulating the expression of antibody to CBir1 flagellin in humans are located within a syntemic region to the major mouse colitogenic locus Cdcs1. *AGA Institute* Abstract #444 p. A-64 2006 (Exhibit 484).

Taylor et al., IL23R haplotypes provide a large population attributable risk for Crohn's disease. *Inflammatory Bowel* vol. 14 pp. 1185-1191 2008 (Exhibit 485).

Taylor et al., Specific clinical and immunological features in Crohn's disease patients are associated with the MHC class III marker Notch4. *Gastroenterology* Abstract 4830 XP001009809 vol. 118 Supp 2 p. A869 2000 (Exhibit 486).

Taylor K et al., Linkage disequilibrium mapping identifies a Class III major histocompatibility complex (MHC) susceptibility haplotypes to Crohn's disease in Ashkenazi Jews. *Am J Human Genetics* Abstract XP001009810 vol. 65 p. A102 1999 (Exhibit 487).

Thisted. What is a P-value? Department of Statistics and health studies. The University of Chicago. May 1998 (Exhibit 488).

Thomas et al., Estrogen and raloxifen activities on amyloid-beta-induced inflammatory reaction. *Microvascular Research* vol. 61 pp. 28-39 2001 (Exhibit 489).

Tomassini, J. E. et al., cDNA cloning reveals that the major group rhinovirus receptor on HeLa cells in intercellular adhesion molecule-1. *Proc. Natl Acad Sci* vol. 86 pp. 4907-4911 1989 (Exhibit 490).

Torok et al., Crohn's disease is associated with a Toll-like receptor-9 polymorphism. *Gastroenterology* vol. 127 pp. 365-368 2004 (Exhibit 491).

Torres et al., The Hermansky-pudlak 1 (HPS1) gene is associated with IBD in Puerto Rico independent of the known HPS1 insertion mutation. Abstract only 2006 Journal unknown (Exhibit 492).

Tountas et al. Heterogenous association between allele 2 of IL-2 receptor antagonist (IL-1RA) and ulcerative colitis in Jewish and non-Jewish populations. Abstract only. *J. Investigative Medicine* XP000673114 vol. 44 1996 (Exhibit 493).

Tountas et al., Genetic association between allele 2 of IL-1 receptor antagonist (IL-1ra) and ulcerative colitis in Los Angeles based hispanic population. Abstract only. *Gastroenterology* XP000673112 vol. 108 1995 (Exhibit 494).

Tountas et al., Increased carriage of allele 2 of IL-1 receptor antagonist (IL-1ra) in Jewish population: the strongest known genetic association in ulcerative colitis. *American Gastroenterology Association* Abstract Only 1996 (Exhibit 495).

Trachtenberg et al., Rare HLA DR-DQ haplotypes associated with inflammatory bowel disease. *Human Immunol* vol. 55 (supp. 1) Abstract #42 p. 59 1997 (Exhibit 496).

Trowsdale et al., Map of the human MHC. *Immunol. Today* vol. 12 pp. 443-446 1991 (Exhibit 497).

Turchan et al., Estrogen protects against the synergistic toxicity by HIV proteins, methamphetamine and cocaine. *BMC Neuroscience* vol. 2 2001 (Exhibit 498).

Udalova, I.A., et al., Highly informative typing of the human TNF locus using six adjacent polymorphic markers *Genomics*, vol. 16 pp. 180-186 1993 (Exhibit 499).

Vaidya et al., The cytotoxic T lymphocyte antigen-4 is a major Graves' disease locus. *Hum Mol Gen* vol. 8 pp. 1195-1199 1999 (Exhibit 500).

Vasiliauskas et al., Marker antibody expression stratifies Crohn's disease into immunilogically homogenous subgroups with distinct clinical characteristics. *Gut* vol. 47 pp. 487-496 2000 (Exhibit 501).

Vasiliauskas et al., Perinuclear antineutrophil cytoplasmic antibodies in patients with Crohn's disease define a clinical subgroups. *Gastroenterology* vol. 110 pp. 1810-1819 1996 (Exhibit 502).

Vavassori et al., CARD15 mutation analysis in an Italian population: Leu1007fsinsC but neither Arg702Trp nor Gly908Arg mutations are associated with Crohn's disease. *Inflamm Bowel Dis* vol. 10 pp. 116-121 2004 (Exhibit 503).

Verdu et al., Modulatory effects of estrogen in two murine models of experimental colitis. *American J Physiology* vol. 283 pp. G27-G36 2002 (Exhibit 504).

Vermiere, S. et al., CARD15 genetic variation in a Quebec population: prevalence, genotype-phenotype relationship and haplotype structure. *Am J Hum Genet* vol. 71 pp. 74-83 2002 (Exhibit 505).

Vermiere, S. et al., Current status of genetics research in inflammatory bowel disease. *Genes and Immunity*, 6:637-645, 2005 (Exhibit 506).

Verthelyi et al. Sex hormone levels correlate with the activity of cytokine-secreting celss in vivo. *Immunology* vol. 100 pp. 384-390 2000 (Exhibit 507).

Voraberger, G. et al., Cloning on the human gene for intercellular adhesion molecule-1 and analysis of its 5'-regulatory region. *J Immunol* vol. 147 pp. 2777-2786 1991 (Exhibit 508).

Warzocha et al., Tumor necrosis factor ligand receptor system can predict treatment outcome of lymphoma patients. *Journal of Clinical Oncology* vol. 15 pp. 499-508 1997 (Exhibit 509).

Webb, G. C., et al., Genetic variability at the human tumor necrosis factor loci. *J. Immunol* vol. 145 pp. 1278-1285 1993 (Exhibit 510).

Weber, J. and May, P., Abundant class of human DNA polymorphisms which can be typed using the polymerase chain reaction. *Am J Hum Genet* vol. 44 pp. 388-396 1989 (Exhibit 511).

Wen et al., TL1A-induced NF-kB activation and c-IAP2 production prevent DR3-mediated apoptosis in TF-1 cells *J of Biological Chemistry* vol. 278 pp. 39251-39258 2003 (Exhibit 512).

Williams et al., Optimization stratagies for the polymerase chain reaction, *Biotechniques*, vol. 7, pp. 762-768 1989 (Exhibit 513).

Wouters et al., Inter- and intraindividual variation of endotoxin- and beta (1->3)-glucan-induced cytokine responses in a whole blood assay. *Toxicology and Industrial Health* vol. 18 pp. 15-27 2002 (Exhibit 514).

Wu et al. Tamoxifen alleviates disease severity and decreases double negative T cells in autoimmune MRL-Ipr/Ipr mice. *Immunology* vol. 100 pp. 110-118 2000 (Exhibit 515).

Wu et al., Tamoxifen decreases renal inflammation and alleviates disease severity in autoimmune NZB/W F1 mice. *Scandinavian Journal of Immunology* vol. 52 pp. 393-400 2000 (Exhibit 516).

Xiao et al., Interaction of Cocksackievirus A21 with its cellular receptor ICAM-1. *J Virol* vol. 75 pp. 2444-2451 2001. (Exhibit 517).

Yamamoto-Furusho et al., Complotype SC30 is associated with susceptibility to develop ulcerative colitis in Mexicans. *J Clin Gasteroenterology* vol. 27 pp. 178-180 1998 (Exhibit 518).

Yamazaki et al., Absence of mutation in the NOD2/CARD15 gene among 483 Japanese patients with Crohn's disease. *Hum Mol Genet* vol. 47 pp. 469-472 2002 (Exhibit 519).

Yamazaki et al., Association analysis of genetic variants in IL23R, ATG16L1 and 5p13.1 loci with Crohn's disease in Japanese patients. *J Hum Genet* vol. 52 pp. 575-582 2007 (Exhibit 520).

Yamazaki et al., Single nucleotide polymorphisms in TNFSF15 confers susceptibility to Crohn's disease. *Hum Mol Genet* vol. 14 pp. 3499-3506 2005 (Exhibit 521).

Yang and Rotter, Genetic aspects of idiopathic inflammatory bowel disease. Kirschner and Shorter (Eds.), *Inflammatory Bowel Disease*Baltimore: Williams and Wilkins pp. 301-331 1195 (Exhibit 522).

Yang et al. The R241 allele if ICAM-1 is associated with a distinct clinical subgroup of Crohn's disease (CD) characterized by perinuclear ANCA (pANCA) production. Abstract only. *American Gasteroenterological Association and American Association for the study of Liver disease.* May 19-22, 1996 (Exhibit 523).

Yang et al., Familial empirical risks for inflammatory bowel disease: differences between Jews and non-Jews. *Gut* vol. 34 pp. 517-524 1993 (Exhibit 524).

Yang et al., Intercellular adhesion molecule 1 gene association with immunologic subsets of inflammatory bowel disease. *Gastroenterology* vol. 109 pp. 440-448 1995 (Exhibit 525).

Yang et al., Linkage of Crohn's disease to the major histocompatibility complex region is detected by multiple non-parametric analyses. *Gut* vol. 44 p. 519-526 1999 (Exhibit 526).

Yang H., et al., Ulcerative colitis: a genetically heterogenous disorder defined by genetic (HLA class II) and subclinical (antineutrophil cytoplasmic antibodies) markers *J. Clin. Invest.*, vol. 92, pp. 1080-1084 1993 (Exhibit 527).

Yang, H. et al., Association of intercellular adhesion molecule-1 (ICAM-1) gene with subsets of Inflammatory Bowel Disease (IBD) stratified by anti-neutrophil cytoplasmic antibodies (ANCAs). *Clinical Research* Abstract only vol. 42 No. 1 pp. 76A 1994 (Exhibit 528).

Yang, H. et al., Genetic Heterogeneity within UC and Crohn's defined by anti-neutrophil cytoplasmic antibodies (ANCAs) and intercellular adhesion molecule-1 (ICAM-1) polymorphisms. *Gastroenterology* vol. 106 No. 4. p. A794 AGA Abstract 1994 (Exhibit 529).

Yoon et al., Decreased potency of the *Vibrio cholerae* sheathed flagellum to trigger host innate immunity. *Infection and Immunity* vol. 76 pp. 1282-1288 2008 (Exhibit 530).

Younes, A. et al., Clinical implication of the tumor necrosis factor family in benign and malignant hematologic disorders. *Cancer* vol. 98 pp. 458-467 2003 (Exhibit 531).

Younes, A. et al., Emerging applications of the tumor necrosis factor family if ligands and receptors in cancer therapy. *J Clin Oncol* vol. 21 pp. 3526-3534 2003 (Exhibit 532).

Zhang et al. Estrogen affects the differentiation and function of splenic monocyte-derived dendritic cells from normal rats. Abstract Only. vol. 20 pp. 129-134 2004 (Exhibit 533).

Zhang et al., Critical role of IL-17 receptor signaling in acute TNBS-induced colitis. *Inflamm Bowel Dis* vol. 12 pp. 382-388 2006 (Exhibit 534).

Ziegler et al., Detectable serum flagellin and liposaccharide and upregulated anti-flagellin and liposaccharide immunoglobulins in human short bowel syndrome. *Am J Physiol Regul Integr Comp Physiol* vol. 294 pp. R402-R410 2008 (Exhibit 535).

Office Action for U.S. Appl. No. 12/528,668 dated Sep. 2, 2011 (Exhibit 536).

Office Action for U.S. Appl. No. 12/529,106 dated Oct. 14, 2011 (Exhibit 537).

Prehn et al., The T Cell Costimulator TL1A Is Induced by Fc R Signaling in Human Monocytes and Dendritic Cells. *J Immunol* vol. 178 pp. 4033-4038 2007 (Exhibit 538).

Takedatsu et al., Linkage of CD-related serological phenotypes: NFKB1 haplotypes are associated with anti-CBir1 & ASCA, and show reduced Nf-κB activation. *Gut* vol. 58 pp. 60-67 2009 (Exhibit 539).

McGovern et al., Genetic epistasis of IL23/1L17 pathway genes in Crohn's disease. *Inflamm Bowel Dis.* vol. 15 pp. 883-889 2009 (Exhibit 540).

Michelsen et al., IBD-Associated TL1A Gene (TNFSF15) Haplotypes Determine Increased Expression of TL1A Protein. PLoS ONE vol. 4 e4719 2009 (Exhibit 541).

Office Action for U.S. Appl. No. 12/527,376 dated Oct. 19, 2011 (Exhibit 542).

Redon et al., Global variation in number in Genome. Nature vol. 444 pp. 444-454 2006 (Exhibit 543).

Zaahl et al., Analysis of the three common mutations in the CARD15 gene (R702W, G908R and 1007fs) in South African colored patients with inflammatory bowel disease. *Molecular and Cellular Probes* pp. 278-281 2005 (Exhibit 544).

* cited by examiner

ILEAL POUCH-ANAL ANASTOMOSIS (IPAA) FACTORS IN THE TREATMENT OF INFLAMMATORY BOWEL DISEASE

This application is the National Phase of International Application PCT/US08/57820, filed Mar. 21, 2008, which designated the U.S. and that International Application was published under PCT Article 21(2) in English. This application also includes a claim of priority under 35 U.S.C. §119(e) to U.S. provisional patent application No. 60/896,171, filed Mar. 21, 2007.

GOVERNMENT LICENSE RIGHTS

The U.S. Government has a paid-up license in this invention and the right in limited circumstances to require the patent owner to license others on reasonable terms as provided for by the terms of Grant No. DK046763 awarded by the National Institutes of Health.

FIELD OF THE INVENTION

The invention relates generally to the fields of inflammation and autoimmunity and autoimmune disease and, more specifically, to ileal pouch-anal anastomosis and genetic methods for diagnosing and treating Inflammatory Bowel Disease.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Crohn's disease (CD) and ulcerative colitis (UC), the two common forms of idiopathic inflammatory bowel disease (IBD), are chronic, relapsing inflammatory disorders of the gastrointestinal tract. Each has a peak age of onset in the second to fourth decades of life and prevalences in European ancestry populations that average approximately 100-150 per 100,000 (D. K. Podolsky, N Engl J Med 347, 417 (2002); E. V. Loftus, Jr., Gastroenterology 126, 1504 (2004)). Although the precise etiology of IBD remains to be elucidated, a widely accepted hypothesis is that ubiquitous, commensal intestinal bacteria trigger an inappropriate, overactive, and ongoing mucosal immune response that mediates intestinal tissue damage in genetically susceptible individuals (D. K. Podolsky, N Engl J Med 347, 417 (2002)). Genetic factors play an important role in IBD pathogenesis, as evidenced by the increased rates of IBD in Ashkenazi Jews, familial aggregation of IBD, and increased concordance for IBD in monozygotic compared to dizygotic twin pairs (S. Vermeire, P. Rutgeerts, Genes Immun 6, 637 (2005)). Moreover, genetic analyses have linked IBD to specific genetic variants, especially CARD15 variants on chromosome 16q12 and the IBD5 haplotype (spanning the organic cation transporters, SLC22A4 and SLC22A5, and other genes) on chromosome 5q31 (S. Vermeire, P. Rutgeerts, Genes Immun 6, 637 (2005); J. P. Hugot et al., Nature 411, 599 (2001); Y. Ogura et al., Nature 411, 603 (2001); J. D. Rioux et al., Nat Genet 29, 223 (2001); V. D. Peltekova et al., Nat Genet 36, 471 (2004)). CD and UC are thought to be related disorders that share some genetic susceptibility loci but differ at others.

A procedure used to treat patients with chronic ulcerative colitis is the ileal pouch-anal anastomosis (IPAA). This is a surgical procedure designed for instances where the entire colon and rectum needs to be removed so that a permanent stoma, opening for collecting waste, can be avoided. Specifically, a pouch is made out of remaining small intestine, which is then pulled through the rectal muscle and sewn to the skin around the anus. After the procedure, when the patient feels the urge to defecate, the rectal muscle contracts and the pouch empties through the anal sphincter.

A common long term problem after IPAA is the inflammation of the pouch, called pouchitis. Additionally, about 5-10% of patients undergoing IPAA with a diagnosis of UC at the time of surgery are subsequently diagnosed with CD. Thus, there is a need in the art to develop predictors of outcome after IPAA.

SUMMARY OF THE INVENTION

Various embodiments provide methods of diagnosing susceptibility to acute pouchitis after ileal pouch anal anastomois for ulcerative colitis in an individual, comprising determining the presence or absence of positive antibody expression of pANCA and Cbir1 in the individual, determining the presence or absence of a low immune reactivity of pANCA and Cbir1, where a low immune reactivity is less than 100 EU/ml in a serum sample taken from the individual, and diagnosing susceptibility to acute pouchitis after ileal pouch anal anastomosis for ulcerative colitis in an individual based upon the presence of a positive antibody expression of pANCA and Cbir1 and the presence of a low immune reactivity of pANCA and Cbir1.

Other embodiments provide methods of diagnosing susceptibility to chronic pouchitis after ileal pouch anal anastomosis for ulcerative colitis in an individual, comprising determining the presence or absence of positive antibody expression of pANCA in the individual, determining the presence or absence of a high immune reactivity of pANCA, where a high immune reactivity is more than 100 EU/ml in a serum sample taken from the individual, and diagnosing susceptibility to chronic pouchitis after ileal pouch anal anastomosis for ulcerative colitis in an individual based upon the presence of a positive antibody expression of pANCA and the presence of a high immune reactivity of pANCA.

Other embodiments provide methods of diagnosing susceptibility to Crohn's Disease after ileal pouch anal anastomosis for ulcerative colitis in an individual, comprising determining the presence or absence of a high immune reactivity of ASCA relative to a healthy subject, determining the presence or absence of a family history of Crohn's Disease, and diagnosing susceptibility to Crohn's Disease after ileal pouch anal anastomosis for ulcerative colitis based upon the presence of a high immune reactivity of ASCA and the presence of a family history of Crohn's Disease.

Other embodiments provide methods of treating pouchitis in an individual, comprising determining the presence of positive antibody expression of pANCA and Cbir1 in the individual, determining the presence of a low immune reactivity of pANCA and Cbir1, where a low immune reactivity is less than 100 EU/ml in a serum sample taken from the individual, and treating the pouchitis in the individual.

Additional embodiments provide methods of treating pouchitis in an individual, comprising determining the presence of positive antibody expression of pANCA in the individual, determining the presence of a high immune reactivity of pANCA, wherein a high immune reactivity is more than 100 EU/ml in a serum sample taken from the individual, and treating the pouchitis in the individual.

Various embodiments also provide methods of treating Crohn's Disease after ileal pouch anal anastomosis for ulcerative colitis in an individual, comprising determining the presence of ASCA sero-positivity, and determining the presence of a family history of Crohn's Disease, and treating the Crohn's Disease after ileal pouch anal anastomosis for ulcerative colitis.

Other embodiments provide methods of determining the prognosis of ulcerative colitis after ileal pouch anal anastomosis ("IPAA") for ulcerative colitis in an individual, comprising, after IPAA, determining the presence or absence of positive antibody expression of pANCA and Cbir1 in the individual, determining the presence or absence of a low immune reactivity of pANCA and Cbir1, where a low immune reactivity is less than 100 EU/ml in a serum sample taken from the individual, and prognosing a complicated case of ulcerative colitis if the individual demonstrates the presence of positive antibody expression of pANCA and Cbir1 and the presence of a low immune reactivity of pANCA and Cbir1. In other embodiments, the complicated case of ulcerative colitis further comprises acute pouchitis.

Various embodiments also provide methods of determining the prognosis of ulcerative colitis after ileal pouch anal anastomosis ("IPAA") for ulcerative colitis in an individual, comprising, after IPAA, determining the presence or absence of positive antibody expression of pANCA in the individual, determining the presence or absence of a high immune reactivity of pANCA in the individual, where a high immune reactivity is more than 100 EU/ml in a serum sample taken from the individual, and prognosing a complicated case of ulcerative colitis if the individual demonstrates the presence of positive antibody expression of pANCA and the presence of a high immunity of pANCA. In other embodiments, the complicated case further comprises chronic pouchitis.

Other features and advantages of the invention will become apparent from the following detailed description, taken in conjunction with the accompanying drawing, which illustrate, by way of example, various embodiments of the invention.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3$^{rd}$ ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

"SNP" as used herein means single nucleotide polymorphism.

"Haplotype" as used herein refers to a set of single nucleotide polymorphisms (SNPs) on a gene or chromatid that are statistically associated.

As used herein, the term "biological sample" means any biological material from which nucleic acid molecules can be prepared. As non-limiting examples, the term material encompasses whole blood, plasma, saliva, cheek swab, or other bodily fluid or tissue that contains nucleic acid.

As used herein, a "family history" means information concerning disorders of those individuals who are direct relatives of a patient, evaluated in an attempt to find out if the patient has hereditary tendencies toward particular diseases. As an example, a family history of Crohn's Disease may be evaluated by multivariate Cox proportional hazards model.

I. Both Preoperative pANCA and Cbir1 Flagellin Expression in Ulcerative Colitis (UC) Patients Influence Pouchitis Development After Ileal Pouch-Anal Anastomosis (IPAA)

As disclosed herein, the inventors assessed the association of preoperative Cbir1 flagellin and pANCA expression on AP or CP development after IPAA for UC. Patients were prospectively assessed for the development of clinically and endoscopically proven AP (antibiotic responsive) or CP (antibiotic dependent or refractory to antibiotic therapy). Sera obtained at time of colectomy in 238 colitis patients were analyzed for ANCA and Cbir using ELISA. pANCA+ patients were sub-stratified into high-level (>100 EU/ml) and lower-level (<100 EU/ml) groups.

As further disclosed herein, there were 171 pANCA+ patients (72%) and 46 Cbir1+ patients (19%). After a median follow-up of 47 months (range, 3-153 mos), 72 patients (30%) developed pouchitis. Median time to diagnosis of pouchitis was 7 months (range, 1-116 mos). Pouchitis developed in 36% of pANCA+ patients vs. 16% of pANCA-patients (p=0.005), 46% of Cbir1+ patients vs. 26% of Cbir1-patients (p=0.02), and 54% of 35 pANCA+/Cbir1+ patients vs. 31% of 136 pANCA+/Cbir1-patients (p=0.02). AP was seen in 43 patients (18%) and CP seen in 29 patients (12%). AP developed in 37 pANCA+ patients (22%) vs. 6 pANCA-patients (9%) (p=0.02), and 12 Cbir1+ patients (26%) vs. 31 Cbir1-patients (16%) (p=0.1). Overall pANCA and Cbir1 were not associated with CP development. Twenty-one patients (12%) were high-level (HL) pANCA+ and 150 patients (88%) were lower-level (LL) pANCA+. Although AP was not influenced by pANCA level, AP was seen in 38% of LL pANCA +/Cbir1+ patients vs. 18% LL pANCA +/Cbir-patients (p=0.03). CP was seen in 29% of HL pANCA+ patients vs. 11% of LL pANCA+ patients (p=0.03). There was no significant difference in CP incidence between HL pANCA+/Cbir+ patients (50%) and LL pANCA+/Cbir-patients (20%) (p=0.3).

As further disclosed herein, both pANCA and Cbir1 expression are associated with pouchitis after IPAA. AP is influenced by both lower-level pANCA+ expression and Cbir1, whereas CP appears to be linked solely to high-level pANCA+ expression. These unique serologic patterns suggest that changes in reactivity to microbial antigens may manifest as different forms of pouchitis after IPAA.

In one embodiment, the present invention provides a method of determining susceptibility to acute pouchitis after ileal pouch anal anastomois for ulcerative colitis in an individual, by determining the presence or absence of positive antibody expression of pANCA and Cbir1 in the individual, determining the presence or absence of a low immune reactivity of pANCA and Cbir1, and diagnosing susceptibility to acute pouchitis after ileal pouch anal anastomosis for ulcerative colitis in an individual based upon the presence of a positive antibody expression of pANCA and Cbir1 and the presence of a low immune reactivity of pANCA and Cbir1. In another embodiment, the present invention provides a method of prognosing ulcerative colitis after ileal pouch anal anastomosis for ulcerative colitis in an individual, by determining the presence or absence of positive antibody expression of pANCA and Cbir1 in the individual, determining the presence or absence of a low immune reactivity of pANCA and Cbir1, and prognosing ulcerative colitis after Heal pouch anal anastomosis for ulcerative colitis, where the presence of a positive antibody expression of pANCA and Cbir1 and the presence of a low immune reactivity of pANCA and Cbir1 is indicative of acute pouchitis. In another embodiment, the present invention provides a method of treating ulcerative colitis by determining the determining the presence of positive antibody expression of pANCA and Cbir1 in the individual, determining the presence of a low immune reactivity of pANCA and Cbir1, and treating the ulcerative colitis.

II. A Prospective Analysis of Predictive Factors for the Diagnosis of Crohn's Disease After Ileal Pouch-Anal Anastomosis for Ulcerative Colitis As disclosed herein, the inventors evaluated the association of preoperative clinical and serologic factors with CD after IPAA in UC. 238 consecutive patients with UC undergoing IPAA at a tertiary referral center were prospectively enrolled into a longitudinally updated database. Demographic and clinical factors were tabulated immediately after surgery. Serum drawn before surgery was assayed for the IBD-associated antibodies anti-Saccharomyces-cerevisiae (ASCA IgG and IgA), anti-outer membrane porin C (OmpC), anti-CBir1 flagellin, and perinuclear antineutrophil cytoplasmic antibody (pANCA) using ELISA. CD was defined by inflammation involving the small-bowel mucosa proximal to the ileal pouch or when a pouch fistula or other perianal complication developed more than 3 months after ileostomy closure. Clinical and serologic predictors were compared using univariate and time-dependent multivariate methods.

As further disclosed herein, sixteen of 238 patients (7%) were diagnosed with CD; 14 underwent IPAA for refractory disease and 2 had surgery for dysplasia. Median time to CD diagnosis was 5 months (range, 1-41 months); median follow-up was 41 months (1-153 months). CD was diagnosed on the basis of afferent ileal limb disease (n=12) and new perianal disease (n=4). Univariate predictors of CD with a p-value $\leq 0.15$ used in the multivariate model included: family history of CD, pre-colectomy platelet count, sero-positivity for ASCA-IgA and pANCA. Multivariate Cox proportional hazards model identified family history of CD (hazard ratio 8.1, 95% confidence interval (CI) 2.6-24.9, p<0.001) and ASCA-IgA sero-positivity (hazard ratio 3.4, 95% CI 1.1-10.5, p=0.03) as the 2 significant factors predictive of CD after IPAA. CD developed in only 8 of 198 (4%) patients without these predictors versus 8 of 40 (20%) in those with at least one of these factors (p=0.002).

As further disclosed herein, patients with UC who have a family history of CD and/or are ASCA-IgA sero-positive before surgery are more likely to be diagnosed with CD after IPAA.

In one embodiment, the present invention provides methods of diagnosing and/or predicting susceptibility to Crohn's Disease in an individual after ileal pouch anal anastomosis by determining the presence or absence in the individual of a family history of Crohn's Disease and/or a high immune reactivity of ASCA relative to a healthy individual, where the presence of a family history of Crohn's Disease and/or a high immune reactivity of ASCA is indicative of susceptibility to Crohn's Disease. In another embodiment, the present invention provides methods of prognosis of ulcerative colitis in an individual by determining the presence or absence in the individual of a family history of Crohn's Disease and/or a high immune reactivity of ASCA relative to a healthy individual, where the presence of a family history of Crohn's Disease and/or a high immune reactivity is indicative of Crohn's Disease after Heal pouch anal anastomosis.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Both Preoperative pANCA and Cbir1 Flagellin Expression in Ulcerative Colitis (UC) Patients Influence Pouchitis Development After Ileal Pouch-Anal Anastomosis (IPAA)

Although most studies of pouchitis after IPAA for UC consider acute pouchitis (AP) and chronic pouchitis (CP) to be a single entity, several lines of evidence suggest that they are distinct disease processes. Antibody responses to microbial antigens define different groups of patients with IBD. Preoperative high-level pANCA (perinuclear antineutrophil cytoplasmic antibody) expression is associated with CP but not AP development. The association of serum responses to Cbir1 flagellin with AP or CP is unknown.

The inventors assessed the association of preoperative Cbir1 flagellin and pANCA expression on AP or CP development after IPAA for UC. Patients were prospectively assessed for the development of clinically and endoscopically proven AP (antibiotic responsive) or CP (antibiotic dependent or refractory to antibiotic therapy). Sera obtained at time of colectomy in 238 colitis patients were analyzed for ANCA and Cbir using ELISA. pANCA+ patients were substratified into high-level (>100 EU/ml) and lower-level (<100 EU/ml) groups.

There were 171 pANCA+ patients (72%) and 46 Cbir1+ patients (19%). After a median follow-up of 47 months (range, 3-153 mos), 72 patients (30%) developed pouchitis. Median time to diagnosis of pouchitis was 7 months (range, 1-116 mos). Pouchitis developed in 36% of pANCA+ patients vs. 16% of pANCA- patients (p=0.005), 46% of Cbir1+ patients vs. 26% of Cbir1-patients (p=0.02), and 54% of 35 pANCA +/Cbir1+ patients vs. 31% of 136 pANCA+/Cbir1-patients (p=0.02). AP was seen in 43 patients (18%) and CP seen in 29 patients (12%). AP developed in 37 pANCA+ patients (22%) vs. 6 pANCA-patients (9%) (p=0.02), and 12 Cbir1+ patients (26%) vs. 31 Cbir1-patients (16%) (p=0.1). Overall pANCA and Cbir1 were not associated with CP development. Twenty-one patients (12%) were high-level (HL) pANCA+ and 150 patients (88%) were lower-level (LL) pANCA+. Although AP was not influenced by pANCA level, AP was seen in 38% of LL pANCA +/Cbir1+ patients vs. 18% LL pANCA +/Cbir-patients (p=0.03). CP was seen in 29% of HL pANCA+ patients vs. 11% of LL pANCA+ patients (p=0.03). There was no significant difference in CP incidence between HL pANCA+/Cbir+ patients (50%) and LL pANCA +/Cbir-patients (20%) (p=0.3).

Both pANCA and Cbir1 expression are associated with pouchitis after IPAA. AP is influenced by both lower-level pANCA+ expression and Cbir1, whereas CP appears to be linked solely to high-level pANCA+ expression. These unique serologic patterns suggest that changes in reactivity to microbial antigens may manifest as different forms of pouchitis after IPAA.

Example 2

A Prospective Analysis of Predictive Factors for the Diagnosis of Crohn's Disease After Ileal Pouch-Anal Anastomosis for Ulcerative Colitis About 5% to 10% of patients undergoing ileal-pouch-anal anastomosis (IPAA) with a diagnosis of ulcerative colitis (UC) at the time of surgery are subsequently diagnosed with Crohn's disease (CD). Predictors for CD post-IPAA have not been prospectively assessed. In this prospective study, the association of preoperative clinical and serologic factors with CD after IPAA in UC was evaluated.

238 consecutive patients with UC undergoing IPAA at a tertiary referral center were prospectively enrolled into a longitudinally updated database. Demographic and clinical factors were tabulated immediately after surgery. Serum drawn before surgery was assayed for the IBD-associated antibodies anti-Saccharomyces-cerevisiae (ASCA IgG and IgA), anti-outer membrane porin C (OmpC), anti-CBir1 flagellin, and perinuclear antineutrophil cytoplasmic antibody (pANCA) using ELISA. CD was defined by inflammation involving the small-bowel mucosa proximal to the ileal pouch or when a pouch fistula or other perianal complication developed more than 3 months after ileostomy closure. Clinical and serologic predictors were compared using univariate and time-dependent multivariate methods.

Sixteen of 238 patients (7%) were diagnosed with CD; 14 underwent IPAA for refractory disease and 2 had surgery for dysplasia. Median time to CD diagnosis was 5 months (range, 1-41 months); median follow-up was 41 months (1-153 months). CD was diagnosed on the basis of afferent ileal limb disease (n=12) and new perianal disease (n=4). Univariate predictors of CD with a p-value$\leq$0.15 used in the multivariate model included: family history of CD, pre-colectomy platelet count, sero-positivity for ASCA-IgA and pANCA. Multivariate Cox proportional hazards model identified family history of CD (hazard ratio 8.1, 95% confidence interval (CI) 2.6-24.9, p<0.001) and ASCA-IgA sero-positivity (hazard ratio 3.4, 95% CI 1.1-10.5, p=0.03) as the 2 significant factors predictive of CD after IPAA. CD developed in only 8 of 198 (4%) patients without these predictors versus 8 of 40 (20%) in those with at least one of these factors (p=0.002).

Patients with UC who have a family history of CD or are ASCA-IgA sero-positive before surgery are more likely to be diagnosed with CD after IPAA.

While the description above refers to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive.

One skilled in the art will recognize many methods and materials similar or equivalent to those described herein, which could be used in the practice of the present invention. Indeed, the present invention is in no way limited to the methods and materials described. Furthermore, one of skill in the art would recognize that the invention can be applied to various inflammatory conditions and disorders and autoimmune diseases besides that of inflammatory bowel disease. It will also be readily apparent to one of skill in the art that the invention can be used in conjunction with a variety of phenotypes, such as serological markers, additional genetic variants, biochemical markers, abnormally expressed biological pathways, and various clinical manifestations.

The invention claimed is:

1. A method of diagnosing susceptibility to acute pouchitis after ileal pouch anal anastomosis for ulcerative colitis in an individual, comprising:
   obtaining a sample from the individual;
   assaying the sample to determine the presence or absence of positive antibody expression of pANCA and Cbir1 in the individual;
   assaying the sample to determine the presence or absence of a low immune reactivity of pANCA,
   wherein a low immune reactivity is less than 100 EU/ml in a serum sample taken from the individual; and
   diagnosing susceptibility to acute pouchitis after ileal pouch anal anastomosis for ulcerative colitis in an individual based upon the presence of a positive antibody expression of pANCA and Cbir1 and the presence of a low immune reactivity of pANCA.

2. A method of treating pouchitis in an individual, comprising:
   obtaining a sample from the individual;
   assaying the sample to determine the presence of positive antibody expression of pANCA and Cbir1 in the individual;
   assaying the sample to determine the presence of a low immune reactivity of pANCA, wherein a low immune reactivity is less than 100 EU/ml in a serum sample taken from the individual;
   diagnosing susceptibility to acute pouchitis after ileal pouch anal anastomosis (IPAA) for ulcerative colitis; and
   treating the pouchitis in the individual based on a diagnosis of susceptibility to acute pouchitis after IPAA for ulcerative colitis.

3. A method of determining the prognosis of ulcerative colitis after ileal pouch anal anastomosis ("IPAA") for ulcerative colitis in an individual, comprising, after IPAA:
   obtaining a sample from the individual;
   assaying the sample to determine the presence or absence of positive antibody expression of pANCA and Cbir1 in the individual;
   assaying the sample to determine the presence or absence of a low immune reactivity of pANCA, wherein a low immune reactivity is less than 100 EU/ml in a serum sample taken from the individual; and
   prognosing a complicated case of ulcerative colitis if the individual demonstrates the presence of positive antibody expression of pANCA and Cbir1 and the presence of a low immune reactivity of pANCA;
   wherein the complicated case of ulcerative colitis further comprises acute pouchitis.

* * * * *